United States Patent
Kitaoka et al.

(10) Patent No.: US 7,407,508 B2
(45) Date of Patent: Aug. 5, 2008

(54) INDWELLING STENT AND LIVING ORGAN DILATOR

(75) Inventors: Takashi Kitaoka, Fujinomiya (JP); Naohisa Okushi, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 303 days.

(21) Appl. No.: 10/671,767

(22) Filed: Sep. 29, 2003

(65) Prior Publication Data
US 2004/0127972 A1 Jul. 1, 2004

(30) Foreign Application Priority Data
Sep. 30, 2002 (JP) .............................. 2002-286647

(51) Int. Cl.
*A61F 2/06* (2006.01)
(52) U.S. Cl. .................................... 623/1.15
(58) Field of Classification Search ................. 623/1.15
See application file for complete search history.

(56) References Cited

U.S. PATENT DOCUMENTS

| | | | | |
|---|---|---|---|---|
| 5,695,516 A | * | 12/1997 | Fischell et al. | 606/194 |
| 5,807,404 A | * | 9/1998 | Richter | 623/1.16 |
| 5,879,381 A | * | 3/1999 | Moriuchi et al. | 623/1.16 |
| 5,931,867 A | * | 8/1999 | Haindl | 623/1.15 |
| 5,968,093 A | | 10/1999 | Kranz | |
| 6,132,460 A | * | 10/2000 | Thompson | 623/1.15 |
| 6,174,326 B1 | * | 1/2001 | Kitaoka et al. | 623/1.15 |
| 6,206,911 B1 | * | 3/2001 | Milo | 623/1.15 |
| 6,293,968 B1 | * | 9/2001 | Taheri | 623/1.15 |
| 6,494,905 B1 | | 12/2002 | Zedler et al. | |
| 6,896,695 B2 | * | 5/2005 | Mueller et al. | 623/1.15 |

FOREIGN PATENT DOCUMENTS

| | | |
|---|---|---|
| EP | 0 795 304 A1 * | 9/1997 |
| EP | 0 832 618 A1 | 4/1998 |
| EP | 0 873 728 A2 | 10/1998 |
| EP | 1 070 513 A1 | 1/2001 |
| JP | 9-299486 A | 11/1997 |
| JP | 2001-161827 A | 6/2001 |
| JP | 2002-172176 | 6/2002 |

\* cited by examiner

*Primary Examiner*—Corrine McDermott
*Assistant Examiner*—Christopher Daniel Prone
(74) *Attorney, Agent, or Firm*—Buchanan Ingersoll & Rooney PC

(57) ABSTRACT

A stent includes annular units arranged in the axial direction of the stent, wherein each of the annular units includes a plurality of annular elements so arranged as to surround the stent axis, the adjacent annular elements being joined to each other through a joint, and the adjacent annular units are interconnected at their joints by at least one link. The annular elements in each annular unit are so arranged that one of the adjacent pair of annular elements is located on the proximal end side in the axial direction of the stent relative to the other of the adjacent pair of annular elements, end portions of each annular unit are projected zigzag, and the zigzag projected end portion of one annular unit is in the state of penetrating into the adjacent annular unit. The joints in each annular unit are substantially parallel to the stent axis.

17 Claims, 17 Drawing Sheets

INDWELLING STENT AND LIVING ORGAN DILATOR

BACKGROUND OF THE INVENTION

The present invention relates to an indwelling stent for use in improving constriction occurred in a living organism such as blood vessel, bile duct, trachea, esophagus, urethra, other organs, etc.

A stent is a generally tubular tool having the function of maintaining a blood vessel or other incised lumen part in an opened state, and is used for improving stenosis of a blood vessel or the like.

Stents are classified, by the function and indwelling method thereof, into self-expandable stents and balloon expandable stents. The balloon expandable stent does not have a self-expanding function, and is used in such a manner that the stent is inserted into a target site, then a balloon is located inside the stent, and the balloon is inflated to expand (plastically deform) the stent by the inflation force of the balloon, thereby bringing the stent into close contact with the inside surface of the target site and fixing the stent there. In this type of stent, the operation of expanding the stent is needed.

A balloon expandable stent has been proposed, for example, in Japanese Patent Laid-open No. 2002-172176 by the present applicant.

The stent disclosed in FIGS. 4, 5 and 6 in the publication is formed in a roughly tubular shape, has a diameter allowing for insertion into a lumen in a living organism, and is expandable when radially outward forces are exerted thereon from the inside of the tubular shape.

The stent comprises a plurality of annular units arranged in the axial direction of the stent, wherein the annular units each comprise a plurality of roughly polygonal filamentous members each of which has a multiplicity of filamentous bent portions and an opening so as to be expandable under radially outward forces and which are joined to each other through a plurality of joints so as to be annular in overall shape. Further, the stent comprises links by which the adjacent annular units are linked to each other through the joints thereof and which are so disposed as not to be continuous with the adjacent links, and a plurality of links are provided between the adjacent annular units at opposed positions or at substantially regular angular intervals around the stent axis.

As shown in FIGS. 4 and 5 and FIG. 6, which is a development of FIG. 4, of the publication, the stent comprises a plurality of the annular units arranged in the axial direction of the stent 10, each of the annular units comprising a plurality of the roughly polygonal filamentous members each of which is elongate in the axial direction of the stent and has filamentous bent portions and a central opening and which are arranged substantially on the circumference of a circle at substantially regular angular intervals around the stent axis, adjacent portions (side portions) in the circumferential direction of the roughly polygonal filamentous members being joined to each other through the joints. Further, the joints of one annular unit and the joints of the adjacent annular unit are linked by the links at two or more locations. From another point of view, the stent 10 is a tubular body composed by linking a multiplicity of the annular units through the links.

A balloon expandable stent has been proposed, for example, in U.S. Pat. No. 5,879,381 by the present applicant.

The stent disclosed in FIGS. 1 to 3 of the publication is a so-called balloon expandale stent which is formed in a roughly tubular shape, has a diameter allowing for insertion into a living organism, and is expandable when radially outward forces are exerted thereon from the inside of the tubular shape. As shown in FIGS. 1 to 3 of the publication, the stent includes annular units arranged in the axial direction of the stent, wherein each annular unit has four roughly elliptic or polygonal annular elements each of which is elongate in the axial direction of the stent and has a central opening and which are arranged substantially on the circumference of a circle at roughly regular angular intervals around the stent axis, adjacent portions (side portions) in the circumferential direction of the annular elements being joined to each other by joints. Further, the adjacent annular units are interconnected at their joints by at least one link.

In general, the balloon expandable stent is produced with a predetermined outside diameter by use of a pipe of a plastically deformable material, a balloon is disposed inside the stent, and the diameter of the stent is reduced by compressing from outside so as to mount the stent onto the balloon. The stents shown in the above-mentioned patent references have the merit that shape retention after expansion is good and the overall length is little changed upon expansion, and have a sufficient effect for dilation of a living organ.

Recently, however, there is a demand for a stent capable of indwelling in a smaller-diameter living organ, particularly, a smaller-diameter blood vessel or bile duct. In the stents disclosed in the above-mentioned patent references, the adjacent roughly polygonal filamentous members or the adjacent roughly elliptic or polygonal annular elements extend in directions orthogonal to the stent axis. Therefore, even though the polygonal filamentous members (polygonal annular elements) can be compressed, it is difficult for the joints to be compressed, so that reduction in diameter by compression is limited, and it is impossible to compress the stent to a sufficiently small diameter.

SUMMARY OF THE INVENTION

It is an object of the present invention to provide a stent which is excellent in shape retention after expansion, is little changed in overall length upon expansion, and is capable of being reduced in diameter, and a living organ dilator using the stent.

In order to attain the above object, according to one aspect of the present invention, there is provided an indwelling stent formed in a substantially tubular shape, having a diameter allowing for insertion into a living organism and expandable when radially outward forces are exerted thereon from the inside of the tubular shape, wherein the stent includes annular units arranged in the axial direction of the stent, each of the annular units includes a plurality of collapsed annular elements so arranged as to surround the stent axis, each of the annular elements is elongate in the axial direction of the stent and has an opening in a central portion thereof, adjacent portions of the annular elements are joined to each other through a joint, the adjacent annular units are interconnected at their joints by at least one link, the annular elements in each annular unit are so arranged that one of each adjacent pair of the annular elements is located on the proximal end side in the axial direction of the stent, end portions of each annular unit are projected zigzag, the zigzag projected end portion of the annular unit is in the state of penetrating into the adjacent annular unit, and the joints in each annular unit are substantially parallel to the stent axis.

In the indwelling stent, one of each adjacent pair of annular elements is located on the proximal end side in the axial direction of the stent, and the joints are substantially parallel to the stent axis, so that the length of the joints does not hamper the compression of the stent. Therefore, the stent can be compressed sufficiently to be small in diameter.

The annular elements are so arranged as to surround the stent axis and are joined to each other by the joints to form the annular unit, and the joints are substantially unchanged upon expansion of the stent. Therefore, the force for expansion will easily be exerted on the center of each annular unit, and each annular unit can be expanded evenly. The links also are substantially unchanged upon expansion of the stent, so that the overall length of the stent is little changed by the expansion of the stent.

In accordance with another aspect of the present invention, there is provided a living organ dilator including a tubular shaft main body, a foldable and expandable balloon provided at a distal end portion of the shaft main body, and a stent so mounted as to envelop the balloon in a folded state and expandable by expanding the balloon, wherein the stent is an indwelling stent according to the one aspect of the present invention.

Since the above-described indwelling stent is used, the living organ dilator can be made small in diameter, and can be inserted into, and expanded in, a living organ which is small in diameter or has a high degree of constriction.

The above and other objects, features and advantages of the present invention will become apparent from the following description and appended claims, taken in conjunction with the accompanying drawings.

DETAILED DESCRIPTION OF THE PREFERRED EMBODIMENTS

Figure 1:
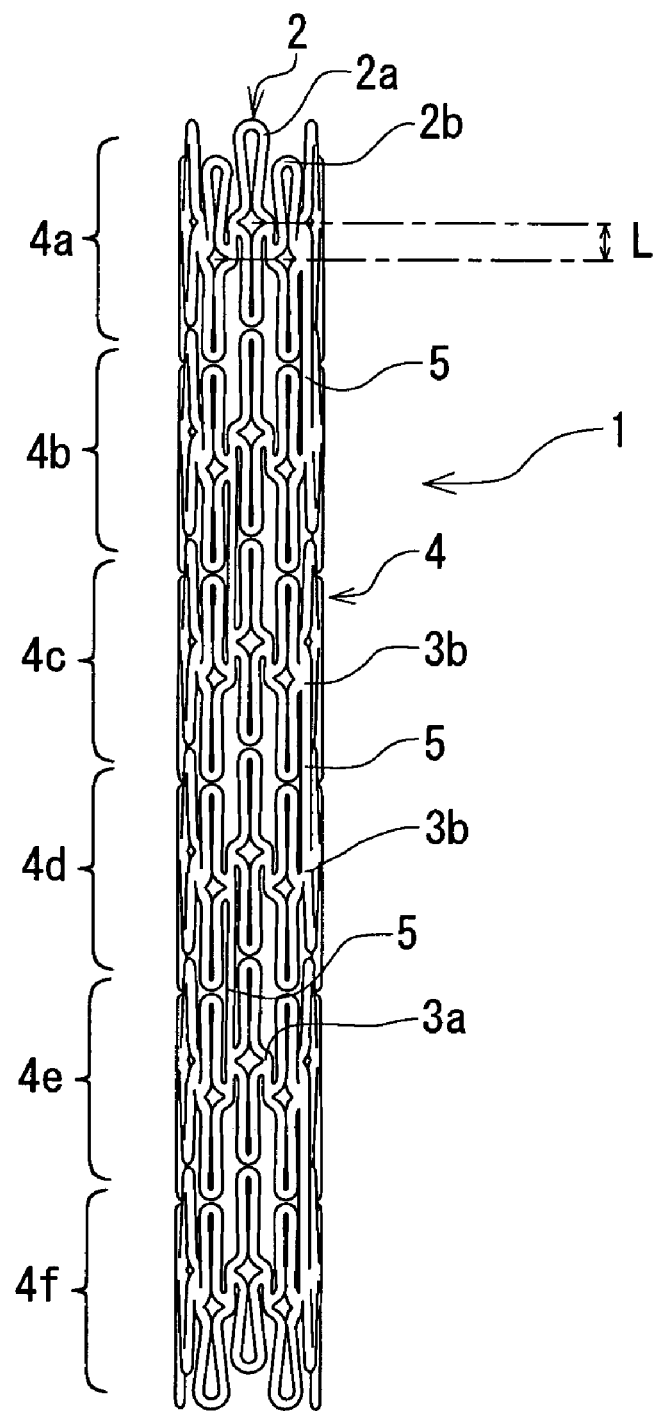
FIG. 1 is a front view, in a compressed state, of a stent according to one embodiment of the present invention.

The stent according to the present invention will be described using one embodiment thereof shown in the drawings.

Figure 2:
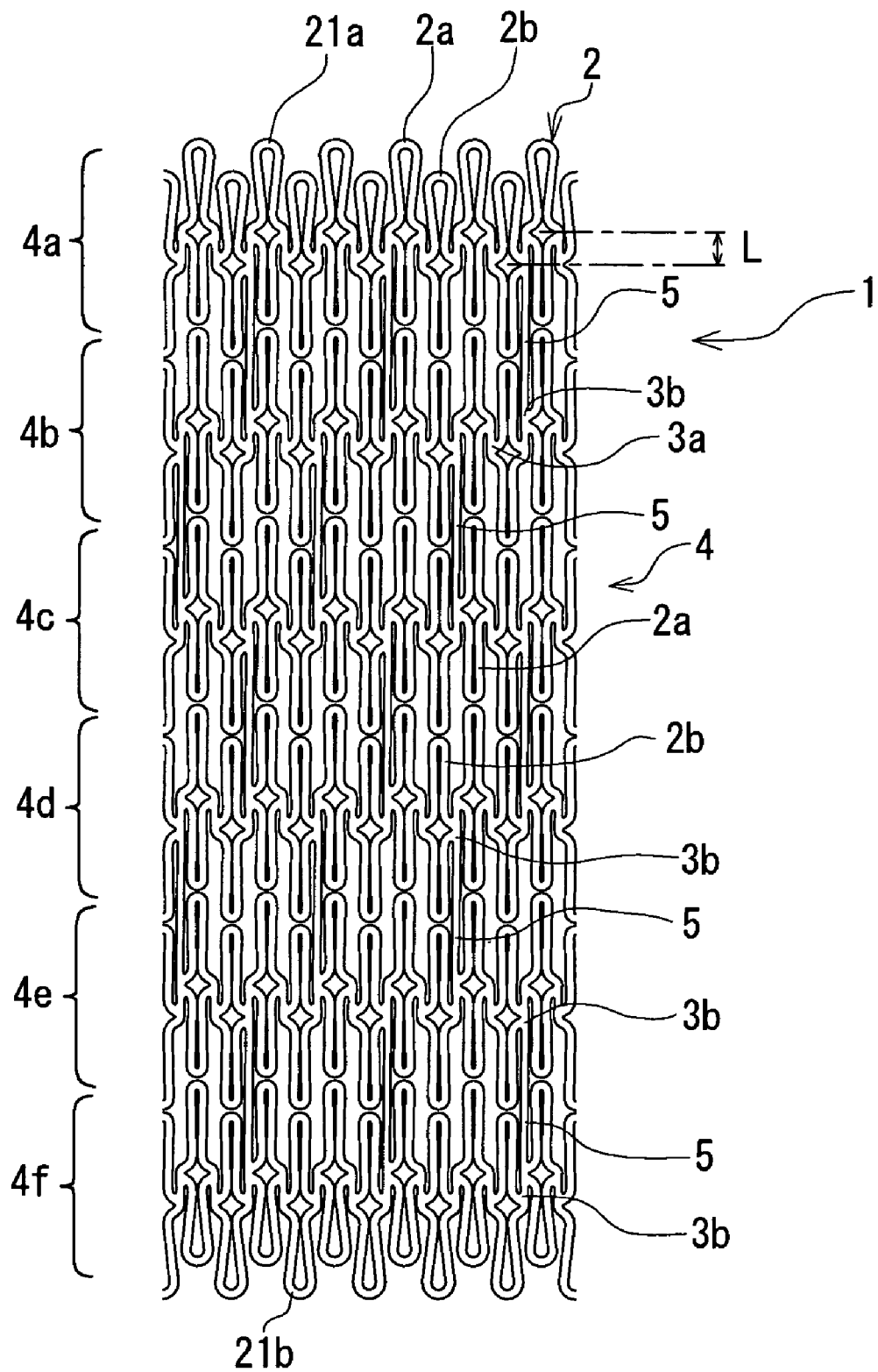
FIG. 2 is a development of the stent shown in FIG. 1.
Figure 3:
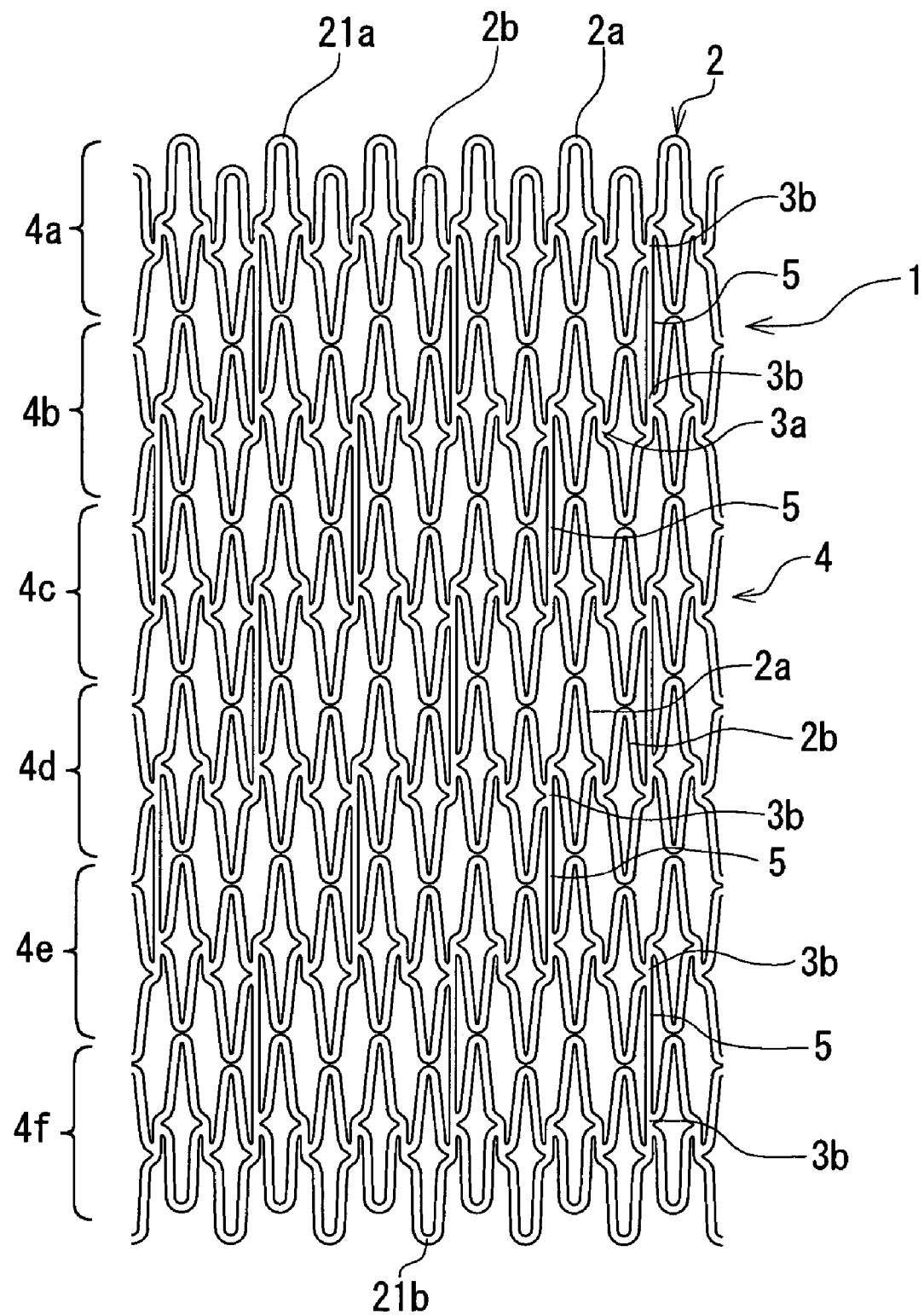
FIG. 3 is a development, at the time of production, of the stent shown in FIG. 1.
Figure 4:
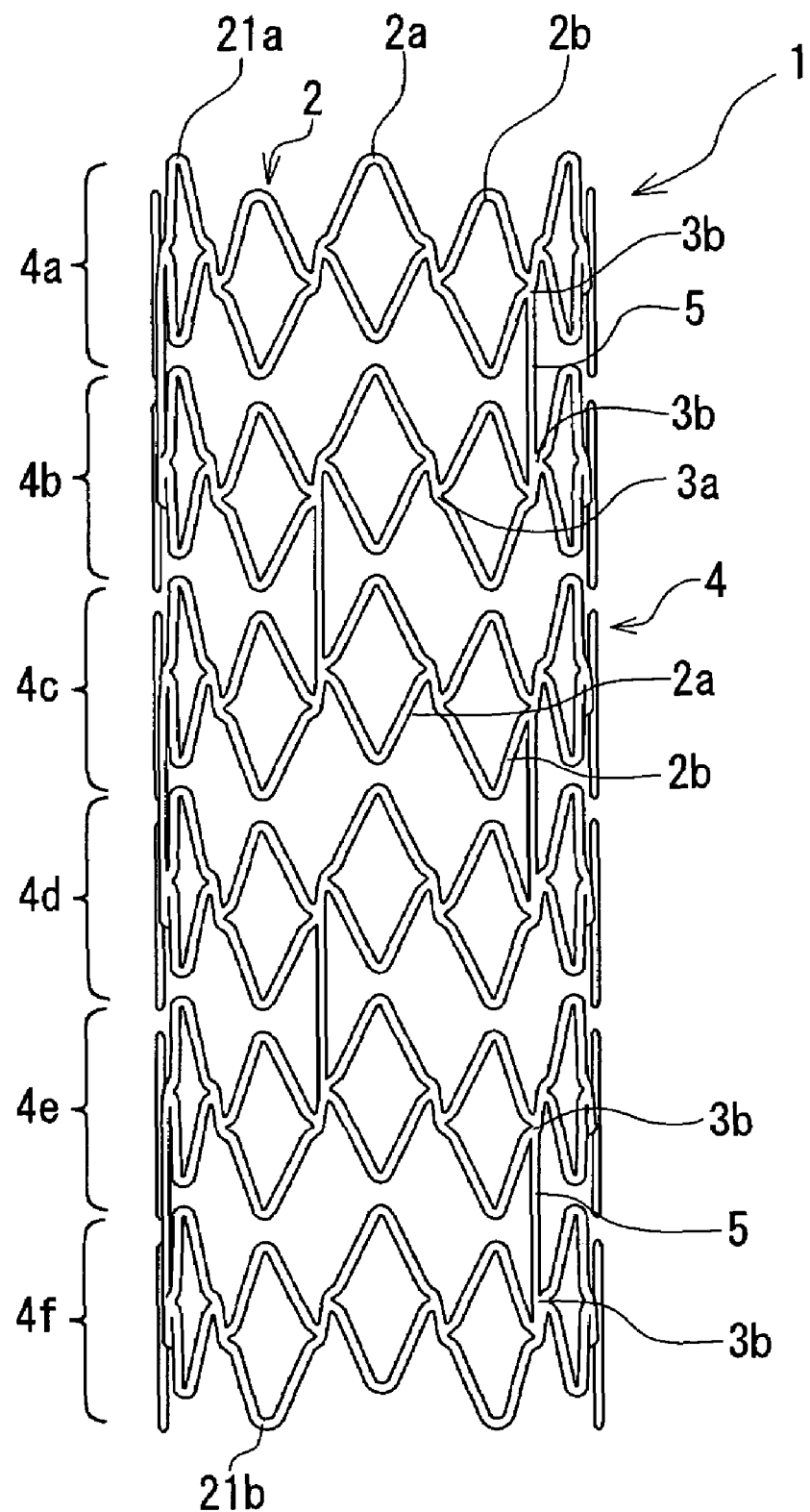
FIG. 4 is a front view, after expansion, of the stent shown in FIG. 1.
Figure 5:
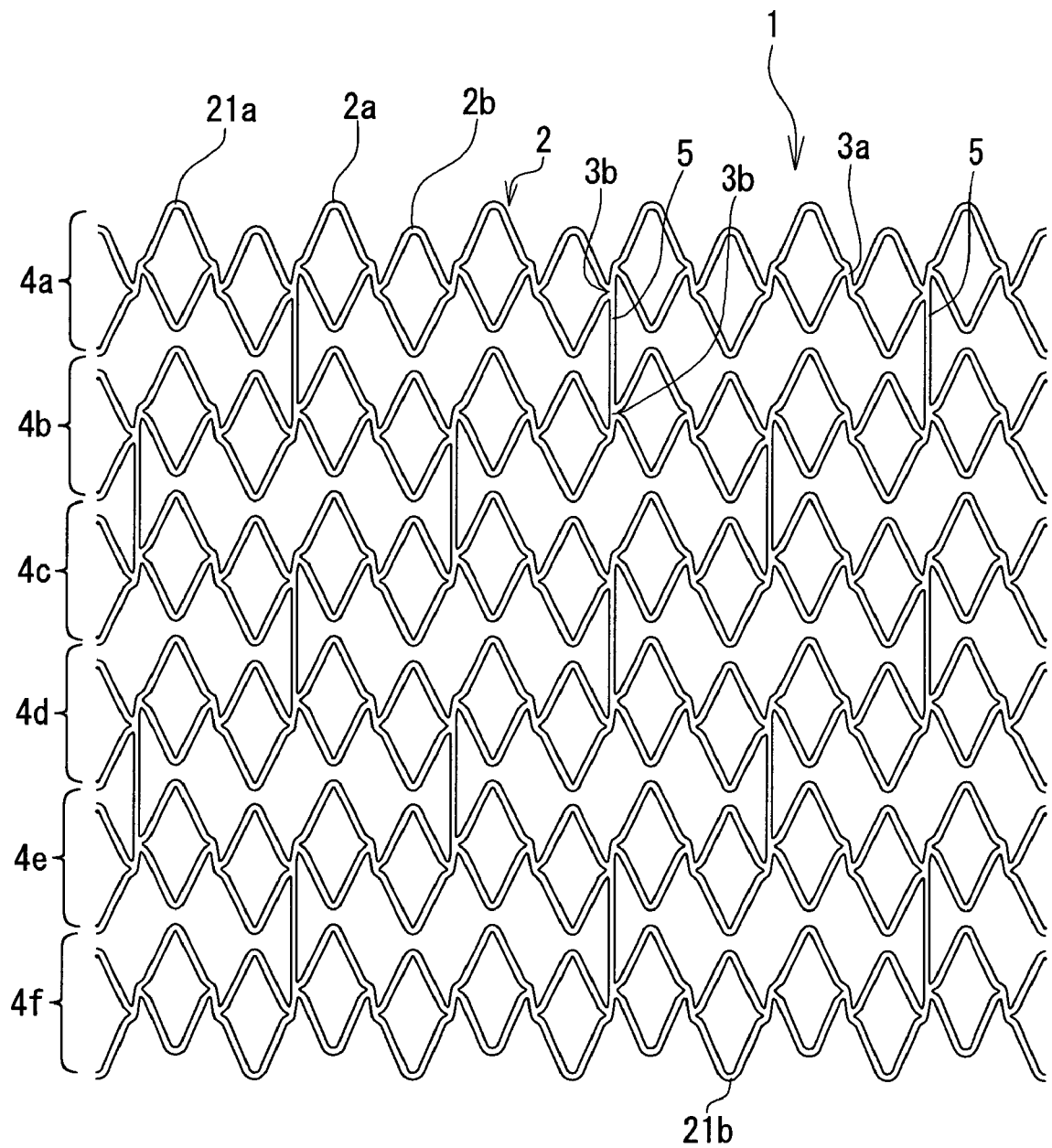
FIG. 5 is a development, after expansion, of the stent shown in FIG. 1.

FIG. 1 is a front view of one embodiment of a stent (in a compressed state) according to the present invention. FIG. 2 is a development of the stent shown in FIG. 1. FIG. 3 is a development, at the time of production, of the stent shown in FIG. 1. FIG. 4 is a front view, after expansion, of the stent shown in FIG. 1. FIG. 5 is a development, after expansion, of the stent shown in FIG. 1.

The stent 1 according to the present invention is a stent which is formed in a roughly tubular shape, has a diameter allowing for insertion into an organism, and is expandable when radially outward forces are exerted thereon from the inside of the tubular shape. The stent 1 includes annular units 4 each having a plurality of collapsed annular elements 2 each of which is elongate in the axial direction of the stent 1 and has a central opening and which are so arranged as to surround the stent axis (or center axis of the stent 1), the adjacent annular elements 2 (2a, 2b) being joined to each other through a joint 3 (3a, 3b). The annular units 4 (4a, 4b, 4c, 4d, 4e, 4f) are arranged in the axial direction of the stent 1, and the adjacent annular units 4 are interconnected at their joints 3 (3a, 3b) by at least one link 5. The joint or joints 3 (3b) of the annular unit 4 and the joint or joints 3 (3b) of the adjacent annular unit 4 are linked to each other by a link or links 5 at least one at location. Further, the annular elements 2 in each of the annular units 4 (4a, 4b, 4c, 4d, 4e, 4f) are so disposed that one 2b of an adjacent pair of the annular elements 2 is located on the proximal end side in the axial direction of the stent 1 relative to the other 2a of the adjacent pair of the annular elements 2, end portions of each annular unit 4 is projected zigzag, and the zigzag projected end portion of each annular unit 4 penetrates into the adjacent annular unit 4. In addition, the joints 3 in each annular unit 4 are substantially parallel to the stent axis.

Thus, the stent 1 is a tubular body composed by linking a multiplicity of the annular units 4 through the links 5.

As shown in FIG. 1, which is a front view of the stent upon compression (in other words, upon attachment onto a balloon), and FIG. 2, which is a development of FIG. 1, the annular unit 4 in this embodiment includes 12 annular elements 2 arranged at nearly regular angular intervals. The annular element 2 is elongate in the axial direction of the stent 1, including an internal opening, and is in a collapsed condition where the opening is narrow. Each annular element 2 is in the shape of an independent closed system, i.e., the annular element 2 is a ring-shaped element opening in a side surface of the stent 1. Since the annular elements 2 have such a shape, they display a strong expansion retention performance. Besides, each annular element 2 is bent in the circumferential direction so that the whole thereof is substantially at an equal distance from the stent axis (the annular unit 4).

In addition, the annular elements 2 in one annular unit 4 are so disposed that one 2b of an adjacent pair of the annular elements 2 is located on the proximal end side in the axial direction of the stent 1 relative to the other 2a of the adjacent pair of the annular elements 2. Namely, end portions of one annular unit 4 are projected zigzag. Specifically, one annular unit 4 includes a plurality of annular elements 2a which have end portions projected to the distal end side, and a plurality of annular elements 2b which have end portions projected to the proximal end side and each of which is located between the annular elements 2a projected to the distal end side. In the stent 1 of this embodiment, each annular unit 4 includes an even number of the annular elements 2, so that every adjacent pair of the annular elements 2a and 2b are staggered from each other along the axial direction. For stabilization of such a zigzag configuration, it is desirable to provide an even number of the annular elements 2.

Further, in each annular unit 4, the adjacent pair of annular elements 2 (2a, 2b) are joined to each other through a short joint 3 (3a, 3b) in the vicinity of the center of a side portion of each annular element 2. In short, the joints 3 (3a, 3b) join the individual annular elements 2 (2a, 2b) to each other in the circumferential direction, to form the annular unit 4. Since joints 3 substantially remain unchanged upon expansion of the stent 1, it is easy for the expanding force to be exerted on the center of each annular element 2, and each annular element 2 can be expanded (deformed) uniformly.

Furthermore, in this stent 1, the joints 3 are substantially parallel to the stent axis. Therefore, at the time of compression of the stent 1, the length of the joints 3 is less liable to restrict the reduction in diameter, so that it is possible to cause the stent 1 to have a small diameter.

The number of the annular elements 2 is not limited to 12, and is preferably not less than four. Particularly, the number of the annular elements 2 is preferably 6 to 20. In addition, the number of the annular elements 2 is preferably an even number. The shape of the annular element 2 is preferably such that the shape upon expansion is roughly elliptic or roughly rhombic; however, other shapes may also be adopted, for example, axially elongate rectangle, hexagon, octagon, etc. A preferable shape is ellipse, in view of stability of deformation at the time of expansion of the stent 1.

The adjacent annular units 4 are interconnected at their joints 3 (3a, 3b) by at least one link 5 which are comparatively long (longer than the joints). Specifically, the annular unit 4a and the adjacent annular unit 4b are mutually linked by the links 5 for connection between the joints 3b, 3b. The annular unit 4b and the adjacent unit 4c are mutually linked by the links 5 for connection between the joints 3b, 3b. The annular unit 4c and the adjacent annular unit 4d are mutually linked by the links 5 for connection between the joints 3b, 3b. The annular unit 4d and the adjacent annular unit 4e are mutually linked by the links 5 for connection between the joints 3b, 3b. The annular unit 4e and the adjacent annular unit 4f are mutually linked by the links 5 for connection between the joints 3b, 3b.

These links 5 substantially remain unchanged upon expansion of the stent 1. Since the links 5 and the joints 3 substantially remain unchanged upon expansion of the stent 1, the overall length of the stent 1 little changes before and after the expansion, and, therefore, the stent 1 would not become extremely short after the expansion thereof. In other words, since the joints 3 joining the annular elements 2 are not moved upon expansion of the stent 1 and the joints 3 are linked by the links 5 parallel to the axis, the overall length of the stent 1 is little shortened.

Incidentally, in each annular unit 4, the joints 3 simply joining the adjacent annular elements 2 are joints 3a, whereas the joints 3 joining the adjacent annular elements 2 and having an end portion of the link 5 are joints 3b.

The links 5 are so provided as to link the adjacent annular units 4 at a plurality of locations. Where the adjacent annular units 4 are linked by two or more links 5, the links 5 are preferably provided at substantially regular angular intervals around the stent axis. Specifically, the stent 1 according to this embodiment is of a type in which the adjacent annular units 4 are linked by three links 5, which are arranged at an angular interval of about 120 degrees around the stent axis. Where two links are provided, the links are preferably disposed at positions opposite to each other, with the stent axis therebetween. A structure in which only one link is provided may also be adopted. The number of the link or links provided between the adjacent annular units is preferably one to five, more preferably one to three.

Further, the links 5 are so arranged that each link is not in continuation with another link adjacent thereto in the axial direction. Therefore, it is possible to restrain the phenomenon in which a load at the time of a deformation of one annular unit 4 to follow up to a deformation of a blood vessel is transmitted directly (or rectilinearly) to other non-adjacent annular units 4, so that the individual annular units 4 can display an independent expansion performance. Furthermore, where the configuration of the links 5 is spiral as viewed for the whole of the stent 1, as in this embodiment, the influences on one annular unit from the non-adjacent annular units are further suppressed.

Besides, in the stent 1 in this embodiment, the annular elements 2 are so aligned as to be substantially rectilinear with respect to the axial direction of the stent 1, as viewed along the axial direction. Specifically, in the stent 1 in this embodiment, all the annular elements 2 adjacent to each other in the axial direction are so aligned as to be substantially rectilinear with respect to the axial direction. Also, all the links 5 are substantially parallel to the axial direction. Therefore, there is little possibility of generation of torsion at the links 5. Further, all the joints 3 are parallel to the axial direction of the stent 1. Therefore, there is little possibility of generation of torsion at the joints 5, either.

Furthermore, when the stent 1 is expanded, the annular elements 2 (2a, 2b) are so deformed that they are pushed open in the vicinity of roughly centers of both side portions in the axial direction, namely, at end portions of the joints. In order to secure this deformation and to cause this deformation to be securely attained at both end portions, both end portions in the axial direction of each of the annular elements 2 (2a, 2b) may be made smaller in sectional area than the other portions. Specifically, it may be considered to set both end portions 21a, 21b in the axial direction to be smaller in width than the other portions, or to set both end portions 21a, 21b in the axial direction to be smaller in material thickness than the other portions.

In addition, the annular elements 2a located on the distal end side in the axial direction of the stent 1 in the annular unit 4 have their end portions penetrating into the annular unit located on the distal end side thereof and adjacent thereto, whereas the annular elements 2b located on the proximal end side in the axial direction of the stent 1 in the annular unit 4 have their end portions penetrating into the annular unit located on the proximal end side thereof and adjacent thereto. Namely, excluding both ends of the stent 1, the projected portions (specifically, end portions of the annular elements 2a) of the zigzag shape of one annular unit are in the state of having penetrated in between the recessed portions (specifically, the annular elements 2b) of the zigzag shape of the adjacent annular unit.

In addition, as the stent 1 (in the compressed state), it is preferable that the links 5 are substantially parallel to the axial direction of the stent 1, as shown in FIGS. 1 and 2. Besides, as the stent 1 (in the compressed state), it is preferable that all the annular elements 2 adjacent to each other in the axial direction are arranged substantially rectilinearly, as shown in FIGS. 1 and 2.

The stent 1 has been produced with a predetermined outside diameter by use of a plastically deformable material-made pipe and then reduced in diameter by compressing from outside. Therefore, the stent 1 has a development, at the time of production, as shown in FIG. 3. At the time of production of the stent 1, each annular element 2 is provided therein with an opening, which is a predetermined void. Upon reduction in diameter by compression, the opening becomes narrow. As shown in FIG. 3, which is a development of the stent 1 at the time of production, it is preferable that the joints 3 are substantially parallel to the axial direction of the stent 1, and the links 5 are also substantially parallel to the axial direction of the stent 1. As shown in FIG. 4, which is a front view upon expansion of the stent 1 of FIG. 1, and in FIG. 5, which is a development of FIG. 4, in the stent 1 of this embodiment the joints 3 and the links 5 are substantially parallel to the axial direction of the stent 1.

The material (plastically deformable material) for forming the stent 1 is preferably a material compatible with organisms to a certain degree. Examples of such a material include stainless steel, tantalum and tantalum alloys, platinum and platinum alloys, gold and gold alloys, cobalt-based alloys, etc. Plating with a noble metal (gold, platinum) after production of the stent shape may also be adopted. A preferable one of stainless steel is SUS316L, which is the most resistant to corrosion.

Further, after the production of the final shape of the stent 1, annealing is preferably conducted. Annealing enhances the flexibility and plasticity of the stent as a whole, leading to good indwelling performance in a bent blood vessel. As compared with the case of not conducting annealing, the annealing reduces the force of restoring to the pre-expansion shape after expansion of the stent, particularly, the force of restoring to a rectilinear shape after expansion of the stent in a bent blood vessel site, whereby it is possible to reduce physical stimulus to the inside wall of the bent blood vessel and to reduce causes of re-constriction. In order to avoid formation of an oxide film on the surface of the stent, it is preferable to carry out the annealing by heating to a temperature of 900 to 1200° C. in an inert gas atmosphere (for example, argon gas), followed by rapid cooling.

The size of the stent 1 at the time of mounting on the balloon (after compression) is preferably as small as possible. The diameter is preferably about 1.2 to 1.8 mm, more preferably 1.3 to 1.6 mm. The length of one annular unit, or the axial length of one annular element, is preferably 1.5 to 4.0 mm, more preferably 2.0 to 3.0 mm. The length by which the end portions of the adjacent annular elements in the annular unit are staggered in the axial direction (in other words, the length L of the axial component between the centers of the adjacent annular elements in the annular unit) is preferably 0.2 to 1.0 mm, the length of the joint 3 in the axial direction is preferably 0.2 to 1.0 mm, and the length of the link 5 in the axial direction is preferably 1.5 to 4.0 mm. The stent 1 preferably includes at least two annular units in the axial direction. Particularly, the number of the annular units is preferably 2 to 40, though dependant on the overall length of the stent. The width of the frame members forming the stent (specifically, the annular elements, joints, and links) is preferably 0.05 to 0.2 mm.

The size of the stent 1 at the time of production (before compression) is as follows. The diameter is preferably 1.0 to 4.0 mm, more preferably 1.2 to 3.0 mm. The length of the annular unit, or the length of one annular element in the axial direction, is preferably 1.5 to 4.0 mm, more preferably 2.0 to 3.0 mm. The length by which the end portions of the adjacent annular elements in the annular unit are staggered in the axial direction (in other words, the length L of the axial component between the centers of the adjacent annular elements in the annular unit) is preferably 0.2 to 1.0 mm, the length of the joint 3 is preferably 0.2 to 1.0 mm, and the length of the link 5 is preferably 1.5 to 4.0 mm.

The stent 1 is preferably provided with a radiopaque material-made marker. It is preferable to provide the radiopaque material-made marker at one end portion of the stent, and it is more preferable to provide the radiopaque material-made markers as both end portions of the stent. More specifically, as in the stent 10 shown in FIG. 6 (development of the stent upon production), a plurality of radiopaque material-made markers 51 are provided in the axial direction on one end side (specifically, the distal end side), and a radiopaque material-made marker 52 is provided also on the other end side (specifically, the proximal end side). This promises easy confirmation of the positions of the end portions of the stent. Particularly, in the stent 10 according to this embodiment, the marker 51 on the distal end side is provided substantially at the distal end of the stent. Further, in the stent 10 in this embodiment, a plurality of markers 52, 53, 54 are provided in the axial direction on the other end side. As a result, the distance from the end portion of the stent can be easily confirmed.

Figure 6:
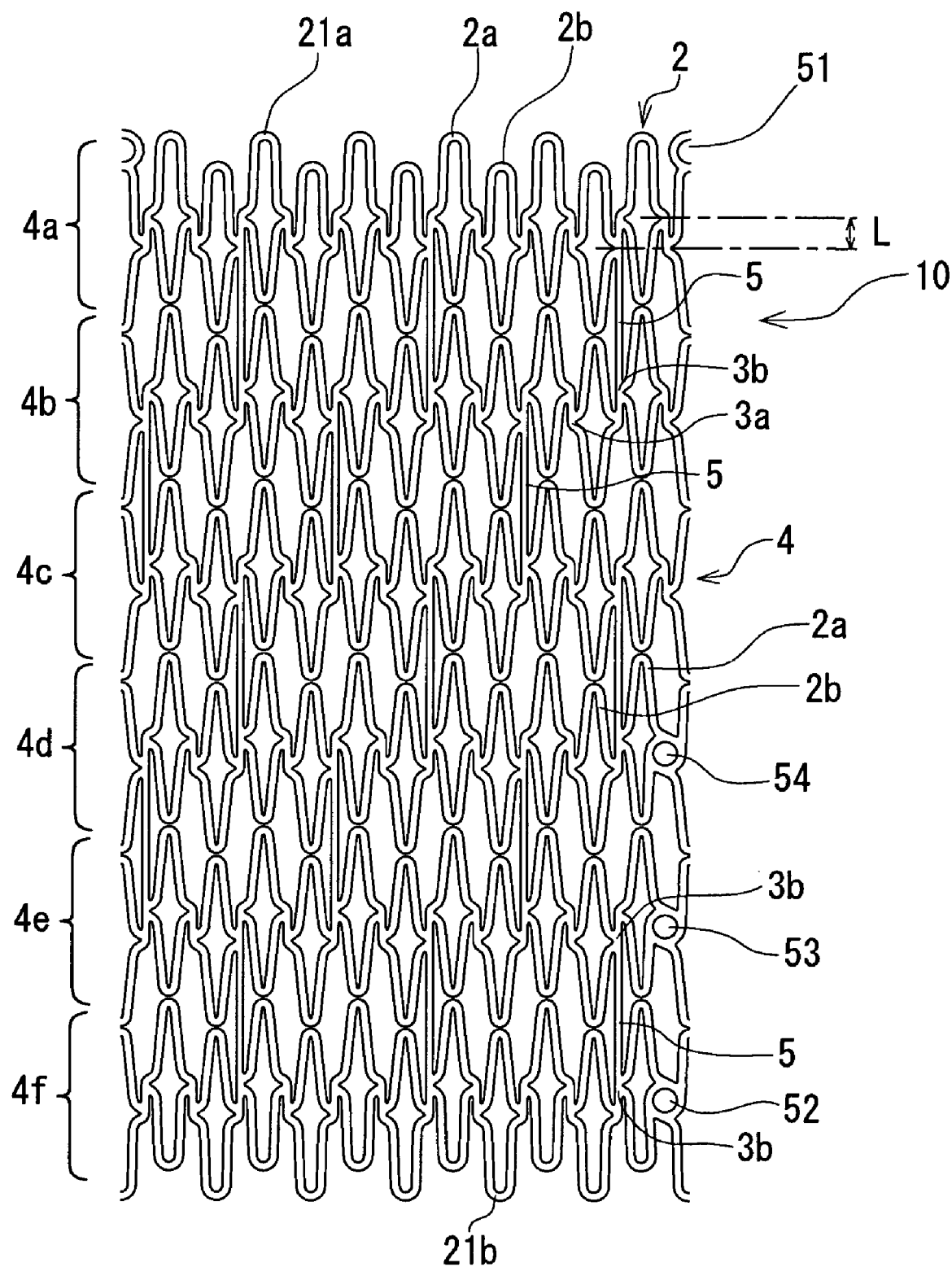
FIG. 6 is a development, at the time of production, of a stent according to another embodiment of the present invention.

As the radiopaque material-made markers 51 and 52, in the embodiment shown in FIG. 6, small openings formed in the stent 10 are plugged with the radiopaque material-made markers, which are fixed to the stent 10. Such a marker is preferably provided, for example, by a method in which a circular disk-like member of a radiopaque material slightly smaller than the small opening formed in the stent 10 is placed in the small opening, and the disk-like member is attached to the stent 10 by caulking it under pressing from both sides. The radiopaque material-made marker is not limited to the above-mentioned but may be any one. For example, the marker may be provided by applying an X-ray contrast material to the outer surface of the stent, by winding a filamentous member formed of an X-ray contrast material, or by attaching a ring-shaped member formed of an X-ray contrast material. Examples of the material for forming the radiopaque material-made marker include gold, platinum, tungsten, alloys thereof, and silver-palladium alloys.

Figure 7:
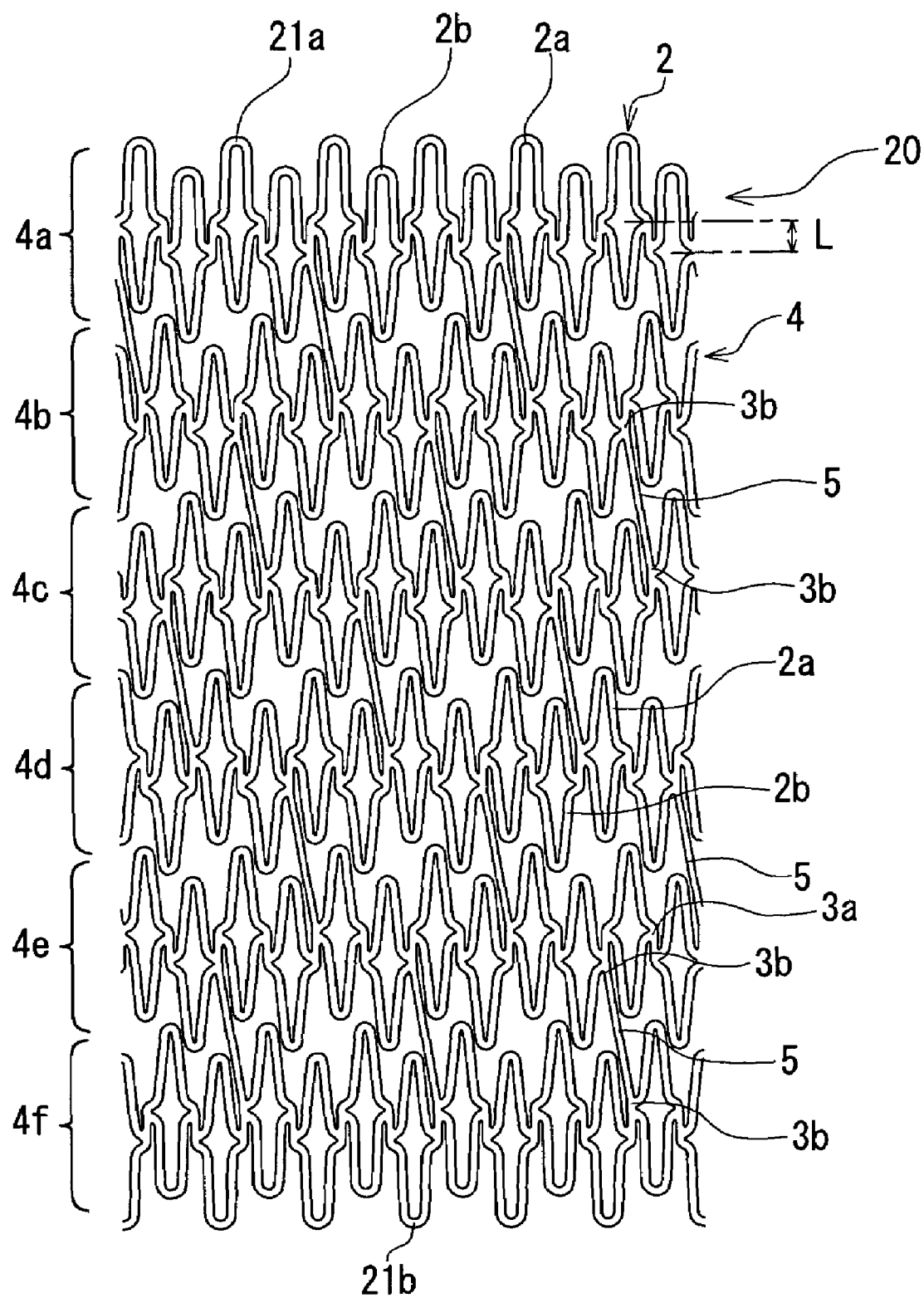
FIG. 7 is a development, at the time of production, of a stent according to a further embodiment of the present invention.
Figure 8:
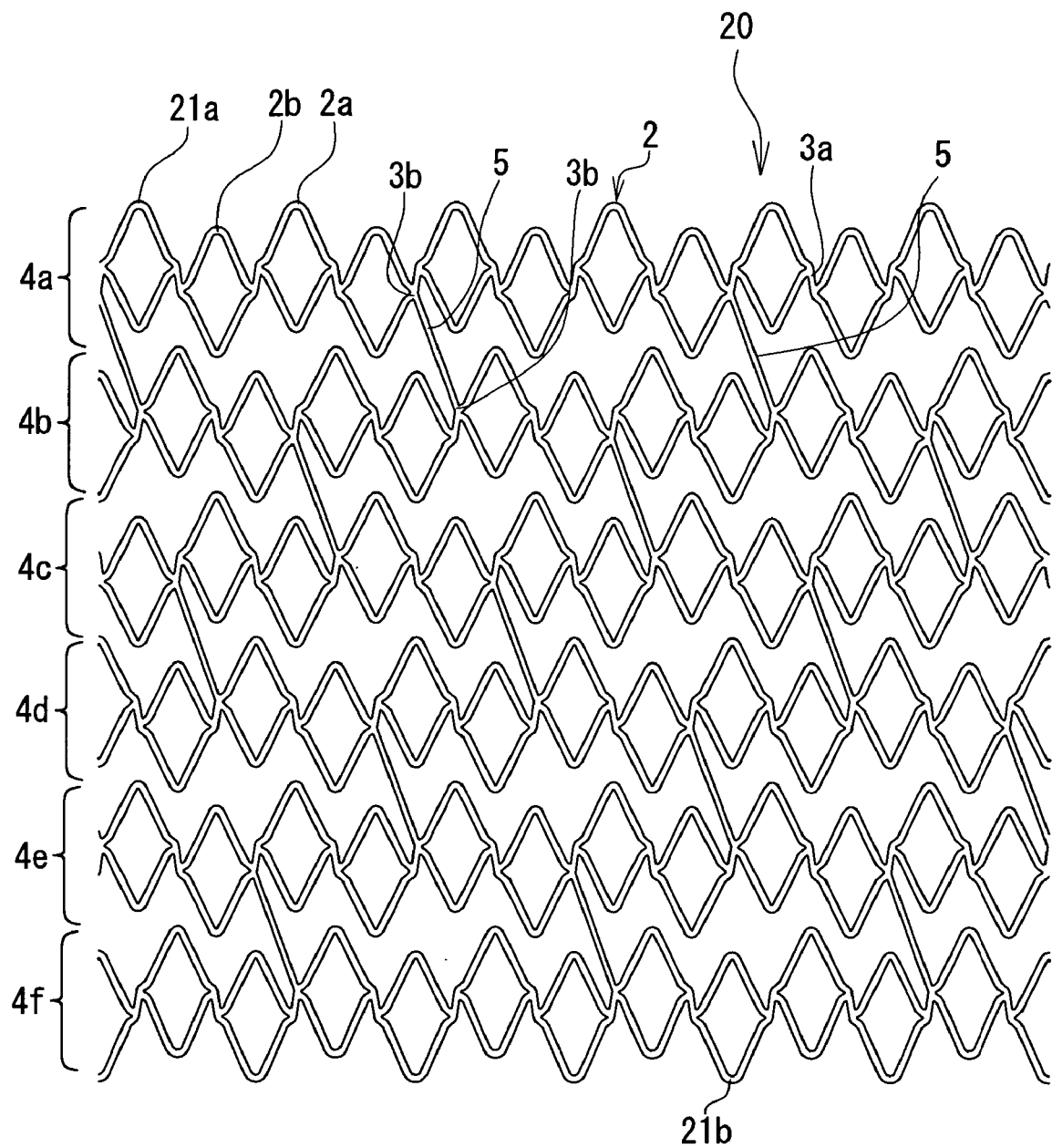
FIG. 8 is a development, in an expanded state, of the stent shown in FIG. 7.

In addition, the stent according to the present invention may be a stent 20 in the form as shown in FIG. 7 (a development upon production). As shown in FIG. 7 and FIG. 8, which is a development of the stent in an expanded state, the stent 20 has a configuration in which the annular elements adjacent to each other in the axial direction are not arranged substantially rectilinearly; specifically, the adjacent annular elements are staggered from each other with reference to the axial direction. In the stent 20 according to this embodiment, the annular elements adjacent to each other in the axial direction are so arranged that the annular element on the proximal end side is located at a position slightly staggered from the position of the annular element on the distal end side, with reference to the stent axis. Namely, the adjacent annular units are arranged as if they have been slightly rotated, one relative to the other, around the stent axis. In other words, the zigzag wave forms formed by the adjacent annular units differ in phase. Incidentally, in the stent 20 in this embodiment, the annular elements in the annular unit on the distal end side and those in the second next annular unit are aligned substantially rectilinearly. Namely, in every other annular unit, the zigzag wave forms formed thereby coincide with each other in phase. Besides, in this stent 20, as shown in FIGS. 7 and 8, the links are inclined by a predetermined angle against the stent axis (or center axis of the stent 20), both upon production and upon expansion.

Figure 9:
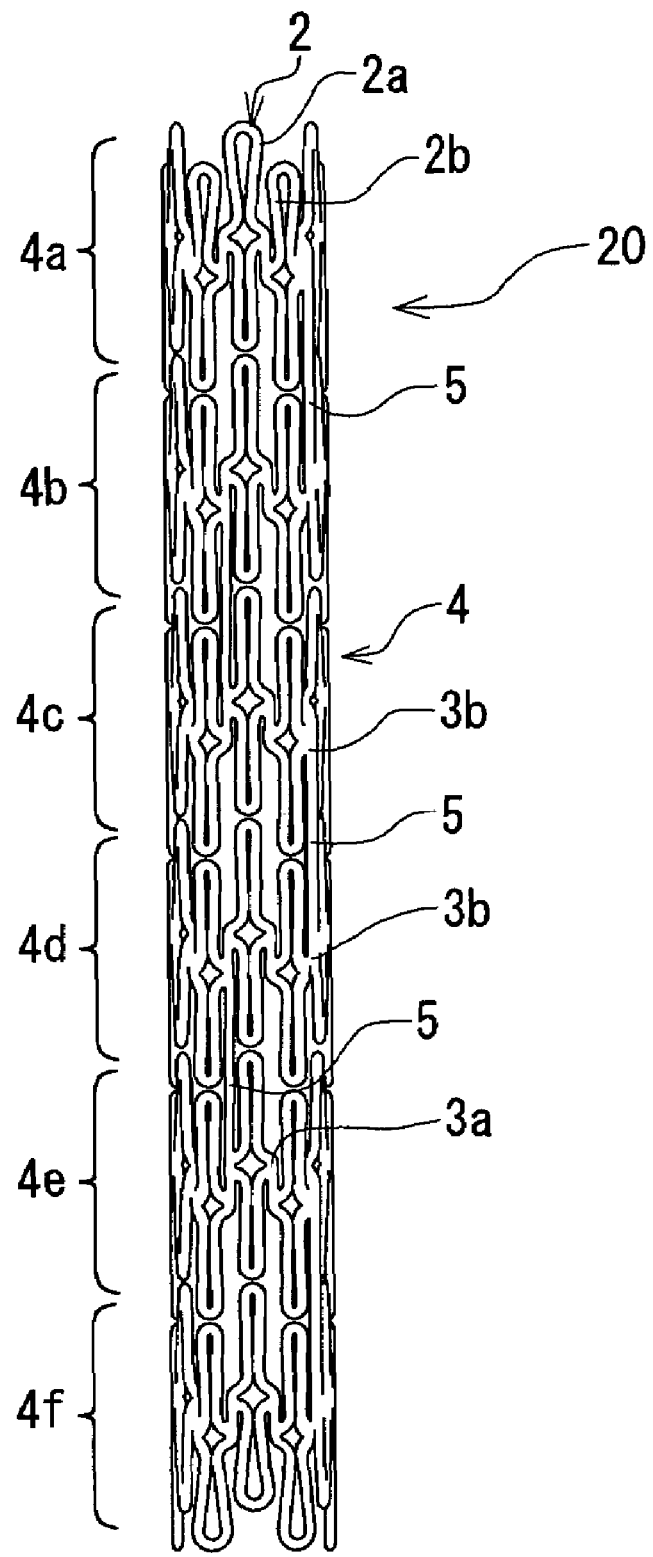
FIG. 9 is a development, in a compressed state, of the stent shown in FIG. 7.

However, even in the case of the stent 20 having such configurations upon production and upon expansion as above-mentioned, when the stent 20 is compressed, the annular elements adjacent to each other in the axial direction come into, or come nearly into, the state of being arranged substantially rectilinearly, and the links come to be substantially parallel to the stent axis, as shown in FIG. 9.

Incidentally, the stent 20 according to this embodiment may also be provided with the radiopaque material-made marker or markers as above-described.

Figure 10:
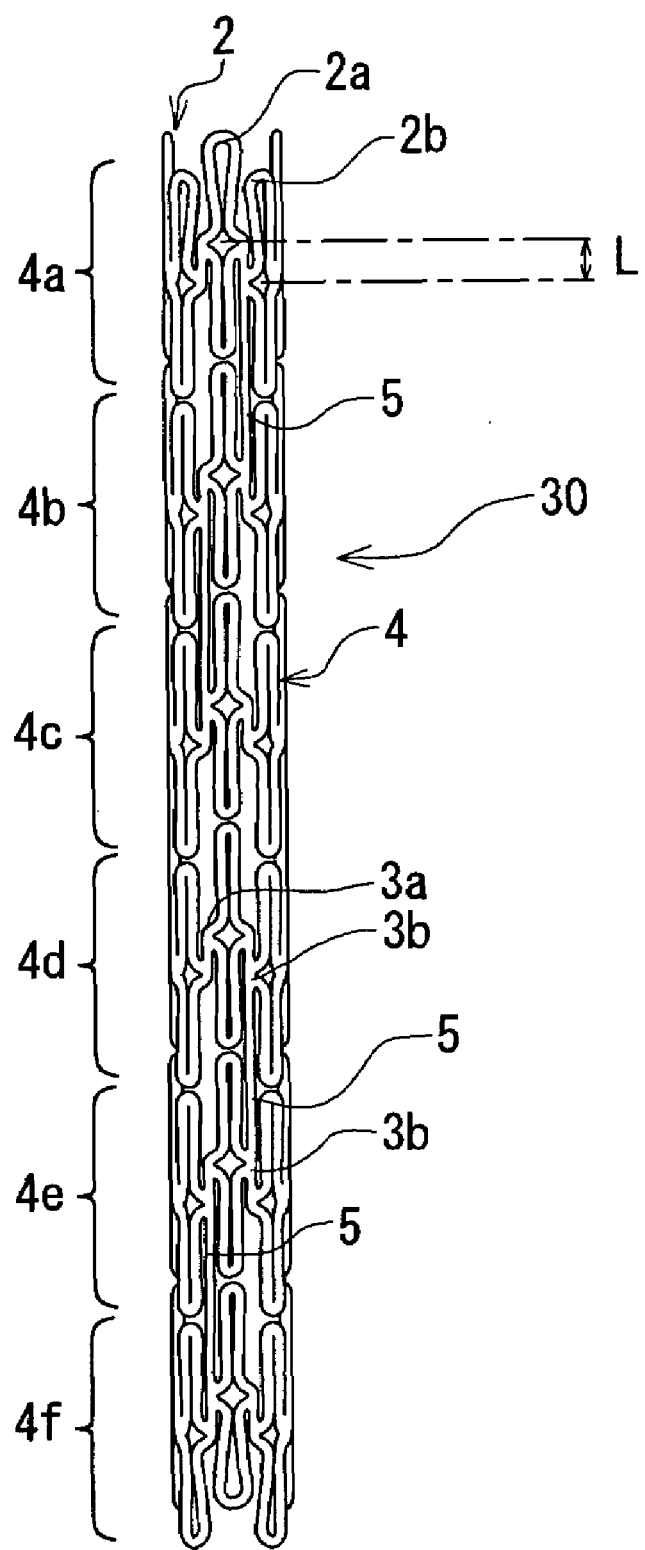
FIG. 10 is a front view, in a compressed state, of a stent according to still another embodiment of the present invention.
Figure 11:
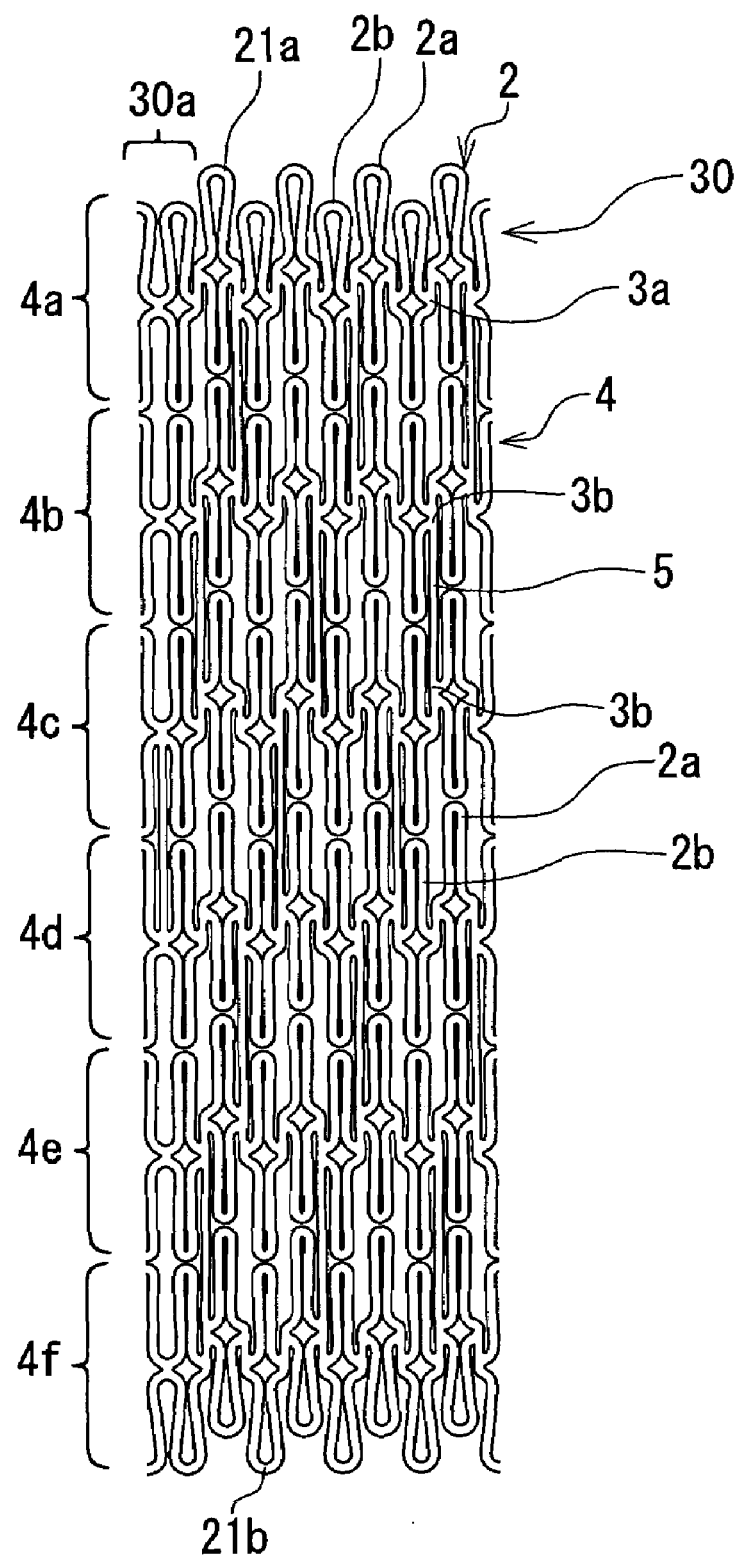
FIG. 11 is a development of the stent shown in FIG. 10.
Figure 12:
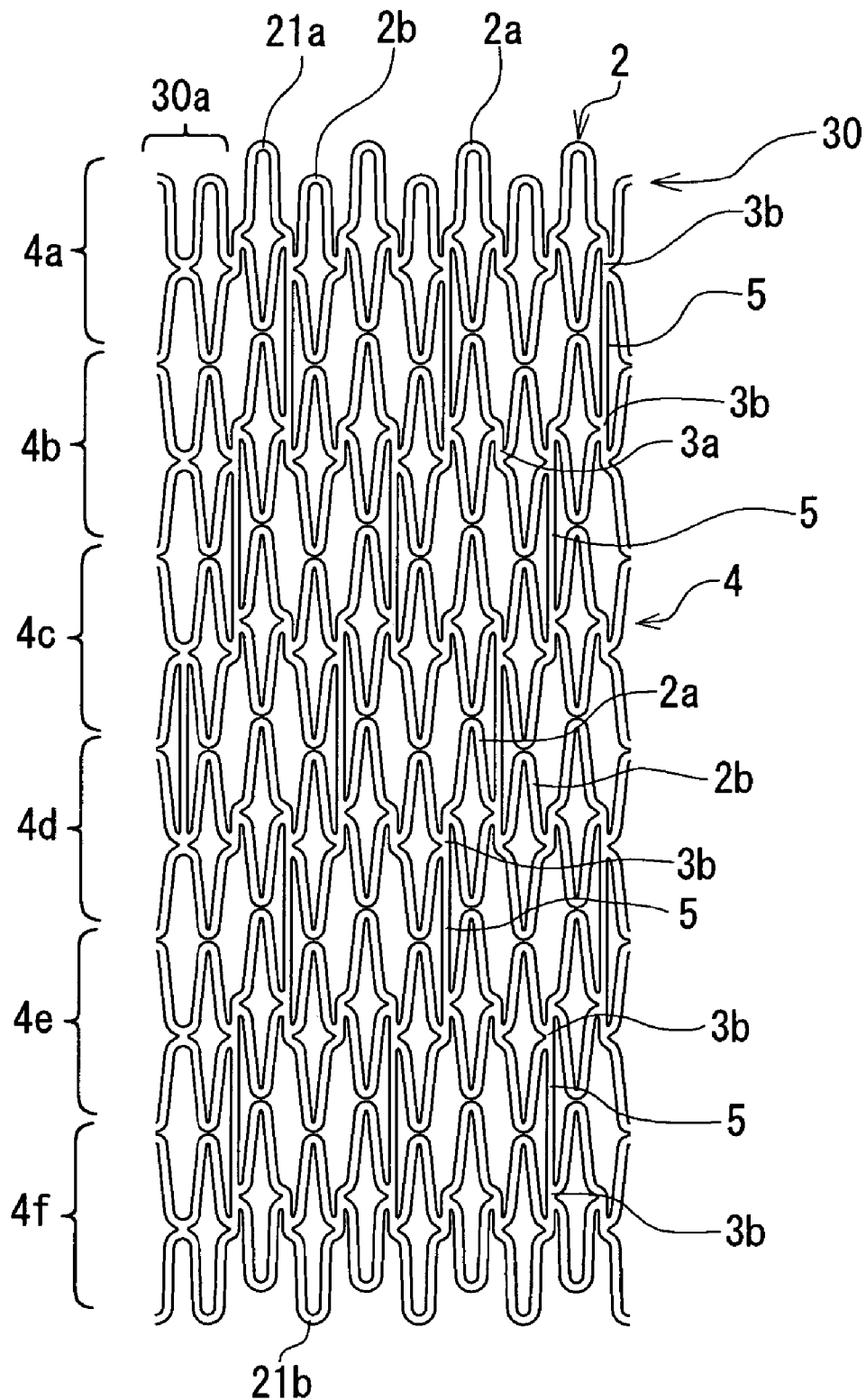
FIG. 12 is a development, at the time of production, of the stent shown in FIG. 10.
Figure 13:
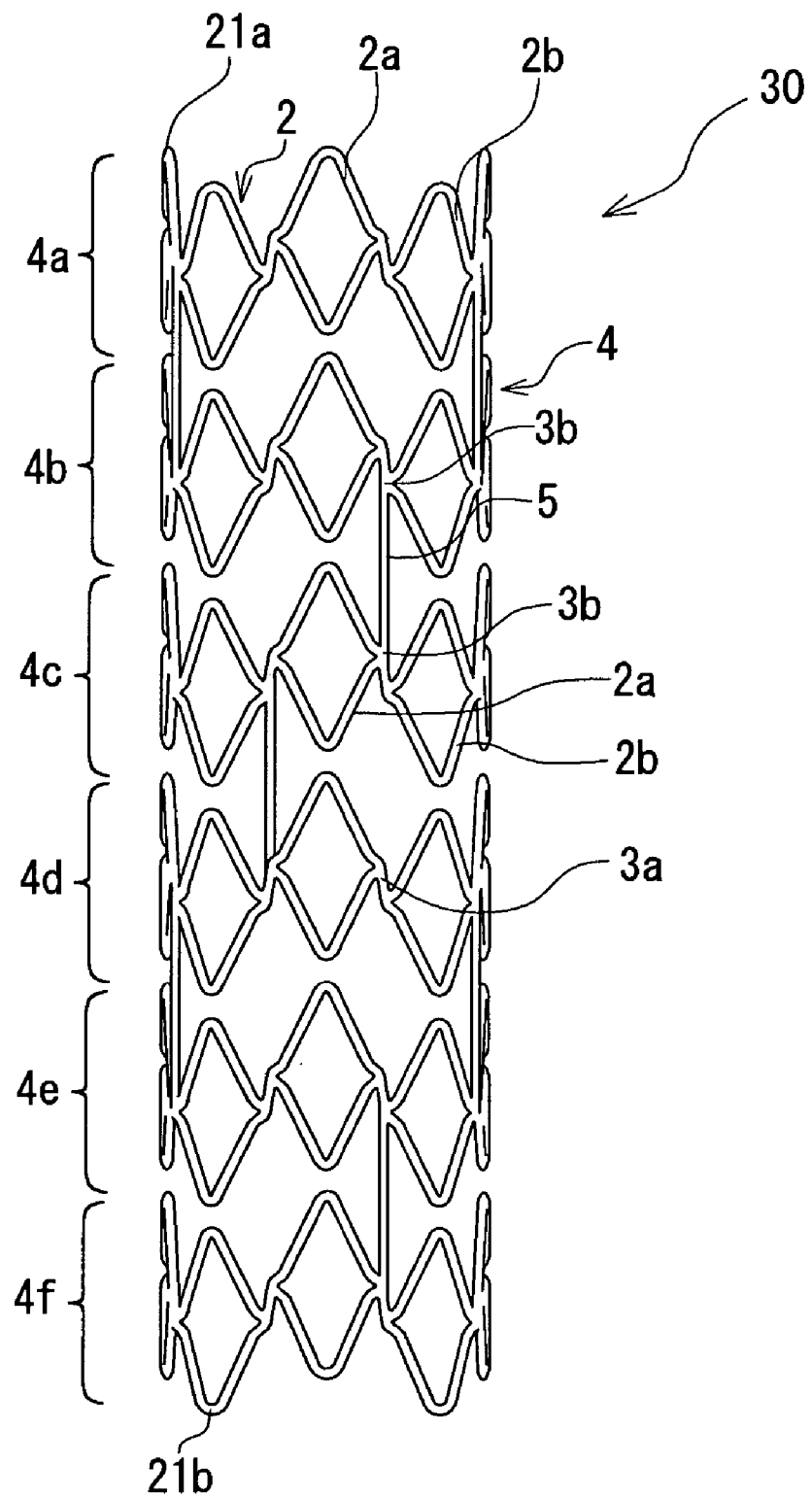
FIG. 13 is a front view, in an expanded state, of the stent shown in FIG. 10.
Figure 14:
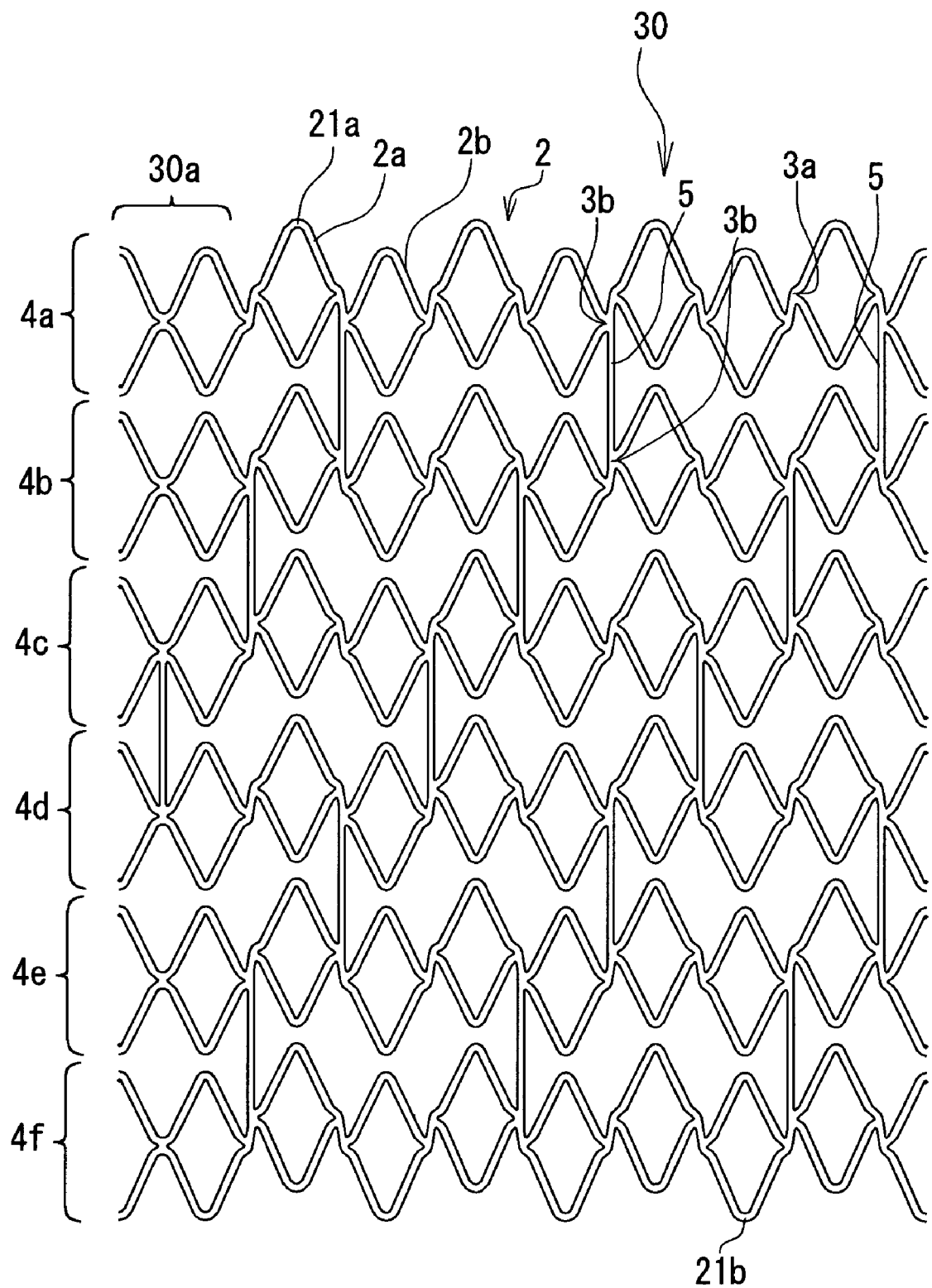
FIG. 14 is a development, in an expanded state, of the stent shown in FIG. 10.

Furthermore, the stent according to the present invention may be a stent 30 in the form as shown in FIG. 10 (a front view in a compressed state) and in FIG. 11, which is a development of FIG. 10. FIG. 12 is a development, upon production, of the stent 30 according to this embodiment; FIG. 13 is a front view of the stent 30 upon expansion; and FIG. 14 is a front view of the stent 30 upon expansion.

The stent 30 in this embodiment differs from the above-described stent 1 in the number of the annular elements in each annular unit. In the sent 30 in this embodiment, one annular unit includes an odd number of the annular elements. Specifically, nine annular elements constitute one annular unit. Therefore, a portion 30*a* where the adjacent annular elements are not staggered from each other in the axial direction is generated at only one location in one annular unit. The other points are the same as in the above-described stent 1. In the stent 30 in this embodiment, also, like in the stent 1, upon compression, upon production and upon expansion, the joints 3 are substantially parallel to the axial direction of the stent 30 and the links 5 are also substantially parallel to the axial direction of the stent 30, as shown in the figures. Further, the stent 30 in this embodiment may also be provided with the radiopaque material-made marker or markers as above-described.

Next, a blood vessel dilator according to the present invention will be described below, using an embodiment shown in the drawings.

Figure 15:
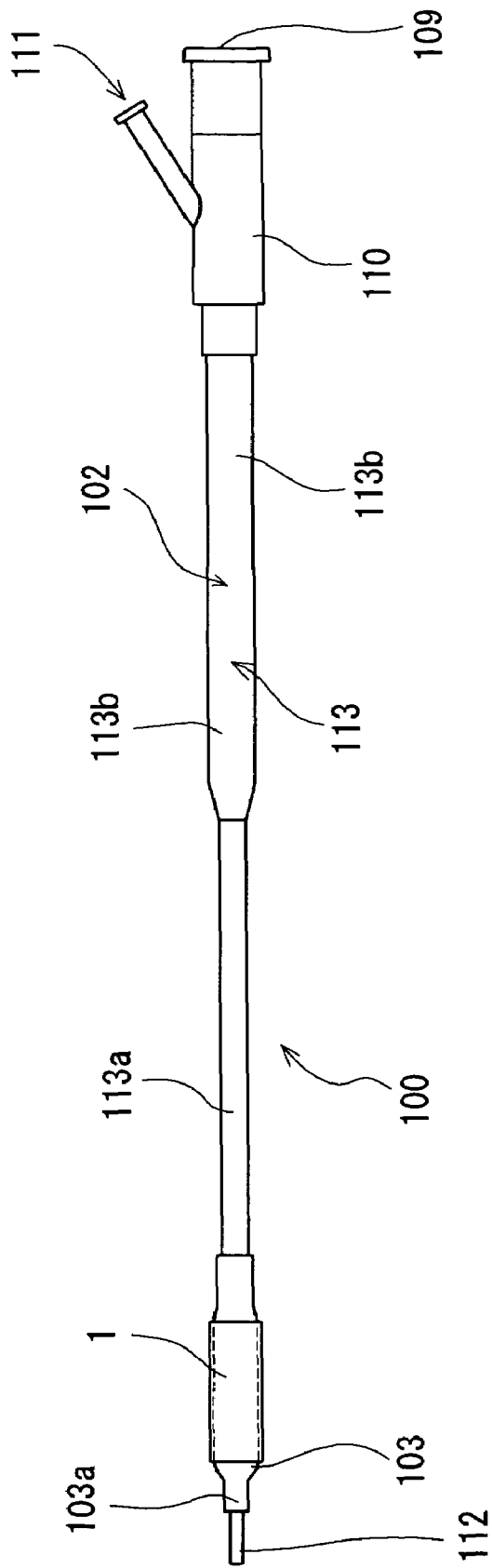
FIG. 15 is a front view of a living organ dilator according to one embodiment of the present invention.
Figure 16:
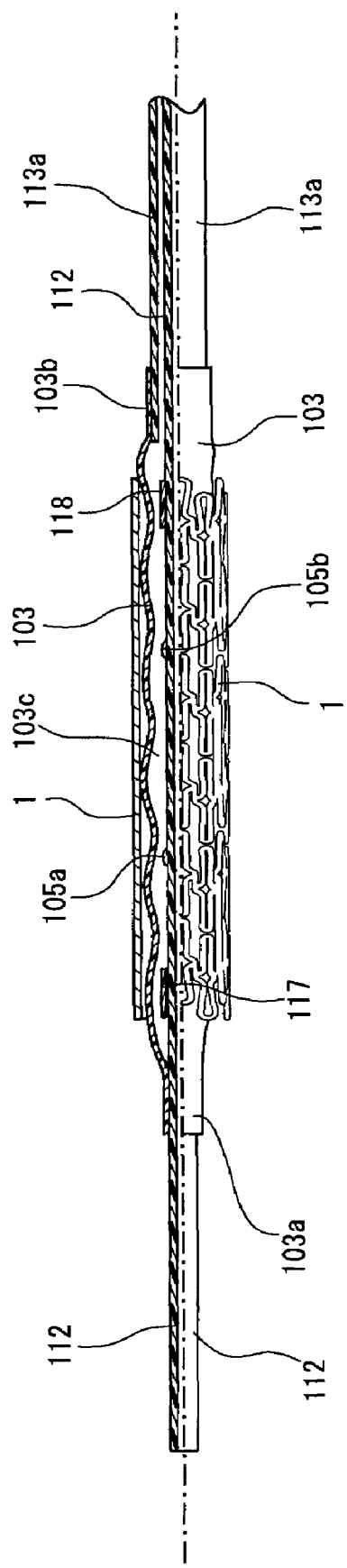
FIG. 16 is an enlarged partial sectional view of a distal end portion of the living organ dilator shown in FIG. 15.
Figure 17:
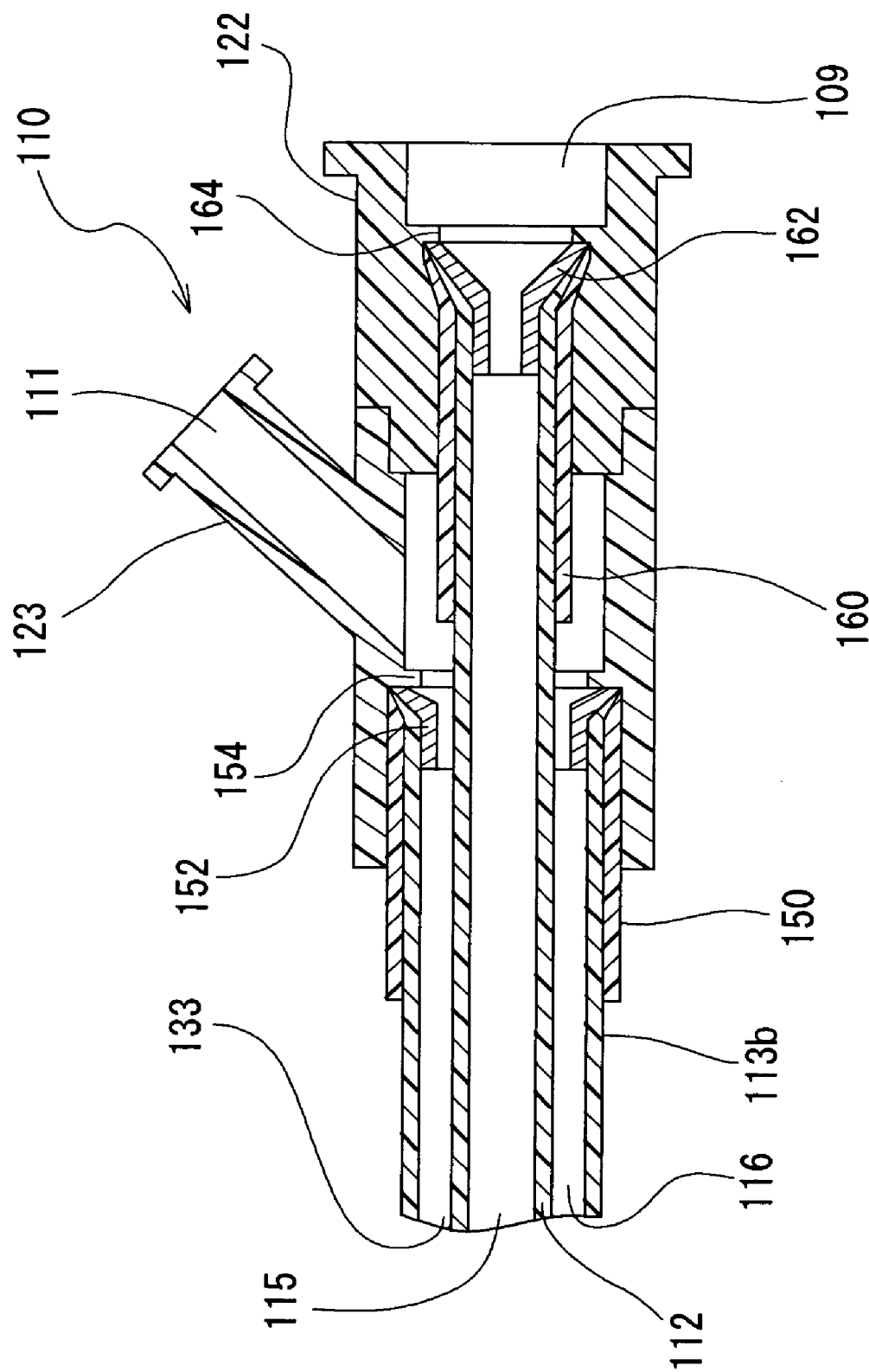
FIG. 17 is an enlarged sectional view of a proximal end portion of the living organ dilator shown in FIG. 15.

FIG. 15 is a front view of a living organ dilator according to one embodiment of the present invention. FIG. 16 is an enlarged partial sectional view of a distal end portion of the living organ dilator shown in FIG. 15. (FIG. 17 is an enlarged sectional view of a proximal end portion of the living organ dilator shown in FIG. 15.)

The blood vessel dilator 100 according to the present invention includes a tubular shaft main body 102, a foldable and expandable balloon 103 provided at a distal end portion of the shaft main body 102, and a stent 1 so mounted (or attached) as to envelop the balloon 103 in the folded state and expandable by the expansion (in other words, inflation) of the balloon 103.

As the stent 1, the above-described stent is used.

As has been described above, the stent 1 is formed in a roughly tubular shape, has a diameter allowing for insertion into an organism, and is expandable when radially outward forces are exerted thereon from the inside of the tubular shape. The stent 1 includes annular units 4 each having a plurality of collapsed annular elements 2 each of which is elongate in the axial direction of the stent 1 and has a central opening and which are so arranged as to surround the stent axis, the adjacent annular elements 2 (2*a*, 2*b*) being joined to each other through a joint 3 (3*a*, 3*b*). In addition, the annular units 4 (4*a*, 4*b*, 4*c*, 4*d*, 4*e*, 4*f*) are arranged in the axial direction of the stent 1, and the adjacent annular units 4 are interconnected at their joints 3 (3*a*, 3*b*) by at least one link 5. Further, the annular elements 2 in each of the annular units 4 (4*a*, 4*b*, 4*c*, 4*d*, 4*e*, 4*f*) are so arranged that one 2*b* of each adjacent pair of the annular elements 2 is located on the proximal end side in the axial direction of the stent 1 relative to the other 2*a* of the adjacent pair of the annular elements 2, end portions of each annular unit 4 is projected zigzag, and the zigzag projected end portion of each annular unit 4 is in the state of having penetrated into the adjacent annular unit. In addition, the joints 3 in each annular unit 4 are substantially parallel to the stent axis.

Furthermore, in the blood vessel dilator 100 according to the present invention, the shaft main body 102 is provided at its one end with a balloon expanding lumen communicated with the inside of the balloon 103. Preferably, the living organ dilator 100 includes a radiopaque material-made member fixed to the outside surface of the shaft main body 102 at a position corresponding to a central portion of the stent 1, or two radiopaque material-made members fixed to the outside surface of the shaft main body 102 at positions corresponding to both ends of a predetermined length of a central portion of the stent 1.

In the living organ dilator 100 in this embodiment, as shown in FIG. 15, the shaft main body 102 includes a guide wire lumen 115 which has one end opened at the distal end of the shaft main body 102 and the other end opened at a proximal end portion of the shaft main body 102.

Thus, the living organ dilator 100 includes the shaft main body 102, the stent expanding balloon 103 fixed at a distal end portion of the shaft main body 102, and the stent 1 mounted onto the balloon 103. The shaft main body 102 includes an inner pipe 112, an outer pipe 113, and a branched hub 110.

As shown in FIGS. 16 and 17, the inner pipe 112 is a tubular member provided therein with the guide wire lumen 115 for passing a guide wire therethrough. The inner pipe 112 has a length of preferably 100 to 2000 mm, more preferably 150 to 1500 mm, an outside diameter of preferably 0.1 to 1.0 mm, more preferably 0.3 to 0.7 mm, and a material thickness of preferably 10 to 150 μm, more preferably 20 to 100 μm. The inner pipe 112 is passed through the inside of the outer pipe 113, and a distal end portion thereof projects from the outer pipe 113. The outside surface of the inner pipe 112 and the inside surface of the outer pipe 113 form the balloon expanding lumen 116, which has a sufficient volume. The outer pipe 113 is a tubular member inside of which the inner pipe 112 is passed and which has its distal end located at a position on the proximal end side relative to the distal end of the inner pipe 112.

The outer pipe 113 has a length of preferably 100 to 2000 mm, more preferably 150 to 1500 mm, an outside diameter of preferably 0.5 to 1.5 mm, more preferably 0.7 to 1.1 mm, and a material thickness of preferably 25 to 200 μm, more preferably 50 to 100 μm.

In the living organ dilator 100 according to this embodiment, the outer pipe 113 includes a distal end side outer pipe 113*a* and a main body side outer pipe 113*b*, which are joined to each other. The distal end side outer pipe 113*a* is reduced in diameter in a tapered form at its portion on the distal end side of the joint with the main body side outer pipe 113*b*, and its portion on the distal end side of the tapered portion has a smaller diameter.

The outside diameter of the smaller-diameter portion of the distal end side outer pipe 113*a* is 0.50 to 1.5 mm, preferably 0.60 to 1.1 mm. The outside diameter of a proximal end portion of the distal end side outer pipe 113*a* and of the main body side outer pipe 113*b* is 0.75 to 1.5 mm, preferably 0.9 to 1.1 mm.

The balloon 103 includes a distal end side joint portion 103*a* and a proximal end side joint portion 103*b*. The distal end side joint portion 103*a* is fixed to the inner pipe 112 at a position slightly on the proximal end side of the distal end of the inner pipe 112, and the proximal end side joint portion 103*b* is fixed to the distal end of the outer pipe 113. In addition, the balloon 103 is communicated with the balloon expanding lumen 116 in the vicinity of a proximal end portion thereof.

The material for forming the inner pipe 112 and the outer pipe 113 is preferably a material having a certain degree of flexibility. Examples of the material which can be used include thermoplastic resins such as polyolefins (for example, polyethylene, polypropylene, ethylene-proplylene copolymers, ethylene-vinyl acetate copolymers; etc.), polyvinyl chloride, polyamide elastomer, and polyurethane, silicone rubber, latex rubber, etc. Among these, preferable are the thermoplastic resins, and more preferable are polyolefins.

The balloon 103 is foldable as shown in FIG. 16, and, in the non-expanded state, it can be folded onto the outer circumference of the inner pipe 112. The balloon 103 has an expandable portion in the form of a substantially fixed-diameter tubular portion (preferably, a cylindrical portion) for enabling expansion of the stent 1 mounted (in other words, attached) thereto. The roughly cylindrical portion may not be a true cylinder but may be a polygonal prismatic portion. In the balloon 103, as above-mentioned, the distal end side joint portion 103a is fixed in a liquid-tight manner to the inner pipe 112, and the proximal end side joint portion 103b to the distal end of the outer pipe 113, by use of an adhesive or by welding. In addition, the balloon 103 is formed in a tapered shape between the expandable portion and the joint portions.

The balloon 103 forms an expansion space 103c between the inside surface of the balloon 103 and the outside surface of the inner pipe 112. The expansion space 103c is communicated with the expanding lumen 116 at a proximal end portion thereof, over the entire circumference thereof.

The material for forming the balloon 103 is preferably a material having a certain degree of flexibility. Examples of the material which can be used include thermoplastic resins such as polyolefines (for example, polyethylene, polypropylene, ethylene-propylene copolymers, ethylene-vinyl acetate copolymers, crosslinked ethylene-vinyl acetate copolymers, etc.), polyvinyl chloride, polyamide elastomer, polyurethane, polyesters (for example, polyethylene terephthalate), and polyarylene sulfides (for example, polyphenylene sulfide), silicone rubber, latex rubber, etc. Particularly, an orientable material is preferred; the balloon 103 is preferably formed of a biaxially oriented material having high strength and high tensile strength.

As for the dimensions of the balloon 103, the cylindrical portion (expandable portion) in an expanded state has an outside diameter of 2 to 4 mm, preferably 2.5 to 3.5 mm, and a length of 10 to 50 mm, preferably 20 to 40 mm. The distal end side joint portion 103a has an outside diameter of 0.9 to 1.5 mm, preferably 1 to 1.3 mm, and a length of 1 to 5 mm, preferably 1 to 1.3 mm. The proximal end side joint portion 103b has an outside diameter of 1 to 1.6 mm, preferably 1.1 to 1.5 mm, and a length of 1 to 5 mm, preferably 2 to 4 mm.

The stent 1 is so mounted as to envelop the balloon 103 which is in the folded state. As the stent, all the stents according to the above-described embodiments can be used. The stent 1 is produced with a predetermined outside diameter by use of a plastically deformable material-made pipe, then the balloon 103 is disposed inside the stent 1, and the stent 1 is reduced in diameter by compressing from outside to be mounted onto the balloon 103.

As shown in FIG. 16, the blood vessel dilator 100 includes two radiopaque material-made members 117 and 118 fixed to the outside surface of the shaft main body 102 at positions corresponding to both ends of the cylindrical portion (expandable portion) in the expanded state. Incidentally, the blood vessel dilator 100 may include two radiopaque material-made members fixed to the outside surface of the shaft main body 102 (in this embodiment, the inner pipe 112) at positions corresponding to both ends of a predetermined length of a central portion of the stent 1. Furthermore, the blood vessel dilator 100 may include a sole radiopaque material-made member fixed to the outside surface of the shaft main body 102 at a position corresponding to a central portion of the stent 1.

The radiopaque material-made members 117 and 118 are preferably ring-shaped members having a predetermined length, coil-shaped windings of a filamentous member, or the like members. Examples of the material usable for the radiopaque material-made members 117 and 118 include gold, platinum, tungsten, alloys thereof, and silver-palladium alloy.

In the living organ dilator 100 according to this embodiment, the branched hub 110 is fixed at the proximal end, as shown in FIG. 17.

The branched hub 110 includes an inner pipe hub 122 which has a guide wire inlet port 109 communicated with the guide wire lumen 115 to form a guide wire port and is attached to the inner pipe 112, and an outer pipe hub 123 which is communicated with the balloon expanding lumen 116, has an injection port 111 and is attached to the outer pipe 113. The outer pipe hub 123 and the inner pipe hub 122 are attached to each other. Thermoplastic resins such as polycarbonate, polyamides, polysulfones, polyarylates, methacrylate-butylene-styrene copolymers, etc. can be preferably used as a material for forming the branched hub 110.

In this embodiment, a bending-preventive tube 150 is provided at a proximal end portion of the outer pipe 113. The bending-preventive tube 150 is fixed to he outer pipe hub 123 by a stopper pin 152. Further, the contact surfaces of the outer pipe 123 and the bending-preventive tube 150 may be coated with an adhesive for attachment.

In addition, a bending-preventive tube 160 is provided at a proximal end portion of the inner pipe 112. The inner pipe 112 fitted with the bending-preventive tube 160 is fixed to the inner pipe hub 122. Further, contact surfaces of the inner pipe hub 122 and the bending-preventive tube 160 may be coated with an adhesive for attachment.

Thermoplastic resins such as polycarbonate, polyamides, polysulfones, polyarylates, methacrylate-butylene-styrene copolymers, etc. can be used as a material for forming the outer pipe hub 123 and the inner pipe hub 122.

The inner pipe hub 122 and the outer pipe hub 123 are fixed to each other. The fixation is carried out by inserting the inner pipe 112 (starting from its distal end) into the outer pipe hub 123 attached to a proximal end portion of the outer pipe 113, from the proximal end of the outer pipe hub 123, and joining them. In this case, joint portions of the inner pipe hub 122 and the outer pipe hub 123 may be coated with an adhesive, whereby they can be securely attached to each other.

Incidentally, the structure of the proximal end of the living organ dilator 100 is not limited to the above-described. For example, instead of providing the branched hub 110, tubes having port members forming openings at the proximal ends may be attached, in a liquid-tight manner, to the guide wire lumen 115 and the balloon expanding lumen 116, respectively.

EXAMPLES

Some specific examples of the stent according to the present invention will be described.

Example 1

A metallic pipe prepared from a stainless steel (SUS316L) pipe having a diameter of 3.0 mm and a material thickness of 0.2 mm by cutting to a length of 18.0 mm was used.

The stent was produced by blanking the stent portion from the metallic pipe. As the method for blanking the stent from the pipe, a variety of methods may be considered. Examples of the method include an etching method called photo-fabrication in which masking and a chemical agent is used, a discharge machining method using a die, and a mechanical cutting method. Here, a laser machining method which is the simplest and high in machining accuracy was used.

As a laser machining apparatus, a YAG laser (a product by NEC Corp.; product code: SL116E) was used. The metallic pipe was set on a motored jig equipped with a chuck mechanism so that offset of axis was not generated, and this assembly was set on an XY table capable of numerical control. The XY table and the motor were connected to a personal computer so that outputs from the personal computer were inputted to a controller for numerical control of the XY table and to the motor. A drawing software was stored in the personal computer, and a development of a stent in the pattern as shown in FIG. 3 was inputted.

By such a configuration, the XY table and the motor are driven based on the drawing data outputted from the personal computer. The metallic pipe was irradiated with a laser beam, to produce the stent.

The laser machining conditions for the metallic pipe were a current of 25 A, an output power of 1.5 W, and a driving speed of 10 mm/min. The system for laser machining is not limited to the above-described, and a so-called laser marker (galvano-meter system) with driving of the laser machining apparatus may also be adopted.

In the stent thus produced, the annular elements were roughly rhombic in shape, with a major-axis length of 2.8 mm and a minor axis of 0.5 mm, and 12 annular elements were arranged at substantially regular angular intervals around the stent axis. In addition, the length by which the end portions of the adjacent annular element in the annular unit are staggered from each other in the axial direction (in other words, the length of the axial component between the centers of the adjacent annular elements in the annular unit) was 0.5 mm, the length of joints 3 extending substantially in parallel to the stent axis was 0.5 mm, and the length of one annular unit in the axial direction was 3.3 mm. The stent including six annular units arranged in the axial direction, had an overall length of 18.0 mm and an outside diameter of 3.0 mm, and the annular units were linked by three links disposed at substantially regular angular intervals around the stent axis. The links extended substantially parallel to the stent axis, and had a length of 2.8 mm. Of the annular units adjacent to each other in the axial direction, the annular unit located on the proximal end side had 0.4 mm projected distal end portions penetrating into the annular unit located on the distal end side. The frame members (annular elements, joints, and links) of the stent had a width of 0.13 mm.

Subsequently, a balloon catheter was inserted into the inside of the stent, and the stent was substantially evenly compressed from outside to be mounted onto the balloon, thereby producing a living organ dilator according to the present invention. The stent thus mounted had an outside diameter of 1.6 mm and a length of 18.0 mm. Each of the annular elements was in a irregular rhombic shape collapsed so that the opening was narrow, and had a major-axis length of 2.8 mm and a minor axis of 0.3 mm. In addition, the length by which the end portions of the adjacent annular elements in the annular unit are staggered from each other in the axial direction (in other words, the length of the axial component between the centers of the adjacent annular elements in the annular unit) was 0.5 mm, the length of the joints 3 extending substantially in parallel to the stent axis was 0.5 mm, and the length of one annular unit in the axial direction was 3.3 mm. Further, of the annular units adjacent to each other in the axial direction, the annular unit located on the proximal end side had the projected distal end portions penetrating, by 0.4 mm, into the annular unit located on the distal end side.

Next, an X-ray contrast agent was injected into the balloon lumen at a pressure of 10 kg/cm$^2$ to inflate the balloon, whereby the stent was expanded substantially evenly. The thus expanded stent had an outside diameter of 6.0 mm. In this instance, the roughly rhombic annular element was deformed into a roughly rhombic shape as shown in FIG. 4, with the major axis reduced from 2.8 mm to about 2.4 mm and the minor axis extended from 0.5 mm to 1.0 mm.

Example 2

A stent was produced in the same manner as in Example 1, except that a development of a stent having the form as shown in FIG. 7 was inputted to the personal computer.

In the stent thus produced, each annular element was roughly rhombic in shape, with a major-axis length of 2.8 mm and a minor axis of 0.5 mm, and 12 annular elements were arranged at substantially regular angular intervals around the stent axis. The length by which the end portions of the adjacent annular elements in the annular unit were staggered from each other in the axial direction (in other words, the length of the axial component between the centers of the adjacent annular elements in the annular unit) was 0.5 mm, the length of the joints 3 extending slantly at a predetermined angle against the stent axis was 0.5 mm, and the length of one annular unit in the axial direction was 3.3 mm. The stent had an overall length of 18.0 mm and an outside diameter of 3.0 mm, comprised six annular units arranged in the axial direction, and the annular units were linked by three links arranged at substantially regular angular intervals around the stent axis. The links extended slantly at a predetermined angle against the stent axis, and had a length of 2.8 mm. Of the annular units adjacent to each other in the axial direction, the annular unit located on the proximal end side had the projected distal end portions penetrating, by 0.4 mm, into the annular unit located on the distal end side. The frame members (annular elements, joins, and links) constituting the stent had a width of 0.13 mm.

Subsequently, a balloon catheter was inserted into the inside of the stent, and the stent was substantially evenly compressed from outside to be mounted onto the balloon, thereby producing a living organ dilator according to the present invention. The stent thus mounted had an outside diameter of 1.6 mm and a length of 18.0 mm. Each annular element was in an irregular rhombic shape collapsed so that the opening was narrow, with a major-axis length of 2.8 mm and a minor axis of 0.3 mm. The length by which the end portions of the adjacent annular elements in the annular unit were staggered from each other in the axial direction (in other words, the length of the axial component between the centers of the adjacent annular elements in the annular unit) was 0.5 mm, the joints had a length of 0.5 mm, the links had been deformed so as to extend substantially in parallel to the stent axis and to have a length of 2.8 mm, and the length of one annular unit in the axial direction was 3.3 mm. In addition, of the annular units adjacent to each other in the axial direction, the annular unit located on the proximal end side had the projected distal end portions penetrating, by 0.4 mm, into the annular unit located on the distal end side.

Next, an X-ray contrast agent was injected into the balloon lumen at a pressure of 10 kg/cm$^2$ to inflate the balloon, whereby the stent was expanded substantially evenly. The stent thus expanded had an outside diameter of 6.0 mm. In this instance, the roughly rhombic annular elements had been deformed into a roughly rhombic shape as shown in FIG. 8, with the major axis reduced from 2.8 mm to about 2.4 mm and the minor axis extended from 0.5 mm to 1.0 mm.

Example 3

A stent was produced in the same manner as in Example 1, except that a development of a stent in the form as shown in FIG. 12 was inputted to the personal computer.

In the stent thus produced, each annular element was roughly rhombic in shape, with a major-axis length of 2.8 mm and a minor axis of 0.5 mm, and nine annular elements were arranged at substantially regular angular intervals around the stent axis. The length by which the end portions of the adjacent annular elements in the annular unit were staggered from each other in the axial direction (in other words, the length of the axial component of the interval between the centers of the adjacent annular elements in the annular unit) was 0.5 mm, the length of the joints 3 extending substantially in parallel to the stent axis was 0.5 mm, and the length of one annular unit in the axial direction was 3.3 mm. The stent had an overall length of 18.0 mm and an outside diameter of 3.0 mm, and the annular units were linked by three links arranged at substantially regular angular intervals around the stent axis. The links extended substantially in parallel to the stent axis, and had a length of 2.8 mm. Of the annular units adjacent to each other in the axial direction, the annular unit located on the proximal end side had the projected distal end portions penetrating, by 0.4 mm, into the annular unit located on the distal end side. In addition, the frame members (annular elements, joints, and links) constituting the stent had a width of 0.13 mm.

Subsequently, a balloon catheter was inserted into the inside of the stent, and the stent was substantially evenly compressed from outside to be mounted onto the balloon, thereby producing a living organ dilator according to the present invention. In the stent thus mounted, each annular element was in an irregular rhombic shape collapsed so that the opening was narrow, with a major-axis length of 2.8 mm and a minor axis of 0.3 mm. The length by which the end portions of the adjacent annular elements in the annular unit were staggered from each other in the axial direction (in other words, the length of the axial component between the centers of the adjacent annular elements in the annular unit) was 0.5 mm, the length of the joints 3 extending substantially in parallel to the stent axis was 0.5 mm, and the length of one annular element in the axial direction was 3.3 mm. Of the annular units adjacent to each other in the axial direction, the annular unit located on the proximal end side had the projected distal end portions penetrating, by 0.4 mm, into the annular unit located on the distal end side.

Next, an X-ray contrast agent was injected into the balloon lumen at a pressure of 10 kg/cm² to inflate the balloon, whereby the stent was expanded substantially evenly. The thus expanded stent had an outside diameter of 4.5 mm. In this instance, the roughly rhombic annular elements had been deformed into a roughly rhombic shape as shown in FIG. 13, with the major axis reduced from 2.8 mm to about 2.4 mm and the minor axis extended from 0.5 mm to 1.0 mm.

(Experiment)

An X-ray contrast agent was injected into the balloon lumen of each of the living organ dilators obtained in Examples 1 and 2 to inflate the balloon, whereby the stent was expanded to have an outside diameter of 6.0 mm. The thus expanded stent was removed from the living organ dilator, one end portion of the stent was fixed, a load was exerted on the stent at a position spaced by 7 mm to the other end side from the fixed boundary, and the load in the condition where the other end was bent downward by 0.5 mm was measured, to observe the degree of flexibility in a direction orthogonal to the axial direction.

As a result, the load was 11.6 gf for the stent of Example 1, and 10.8 gf for the stent of Example 2. Thus, these stents showed sufficient flexibility, although the annular units were linked by the three links.

In the stent according to the present invention, one of the adjacent pair of the annular elements is located on the proximal end side in the axial direction of the stent, and the joints are substantially parallel to the stent axis, so that the length of the joints is less liable to cause a trouble at the time of compressing the stent. Therefore, the stent can be compressed sufficiently, and can be made small in diameter.

Further, since the annular elements constituting individually independent closed systems with the roughly elliptic or roughly polygonal shape and the center opening are joined along the circumferential direction, a strong expansion retention force is displayed. In addition, the center of a side portion in the axial direction of the stent of one annular element and the center of a side portion in the axial direction of the stent of the adjacent annular element are joined to each other through the short joint, and the joints remain substantially unchanged upon expansion of the stent. Therefore, the force of expansion would easily be exerted on the center of each annular element, and each annular element can be expanded evenly. The adjacent annular units are interconnected at their joints by at least one link, and the links also remain substantially unchanged upon expansion of the stent. Therefore, the overall length of the stent is little changed by the expansion of the stent.

Further, where the links are substantially parallel to the stent axis, the joints are less liable to cause a trouble at the time of compressing the stent, so that the stent can be compressed sufficiently and can be made small in diameter.

Besides, the living organ dilator according to the present invention includes the tubular shaft main body, the foldable and expandable balloon provided at a distal end portion of the shaft main body, and the stent so mounted as to envelop the balloon in the folded state and expanded by the expansion of the balloon, wherein the above-described stent is used as the stent of the living organ dilator.

Since the above-described stent is used, the living organ dilator can be made small in diameter, and can be inserted into, and expanded in, a living organ which is small in diameter or has a high degree of constriction.

The present invention is not limited to the details of the above described embodiments. The scope of the invention is defined by the appended claims and all changes and modifications as fall within the equivalence of the scope of the claims are therefore to be embraced by the invention.

What is claimed is:

1. An indwelling stent formed in a substantially tubular shape, having a diameter allowing for insertion into a living organism and expandable when radially outward forces are exerted thereon from the inside of the tubular shape, wherein said stent comprises annular units arranged in an axial direction of said stent, each of said annular units comprises a plurality of collapsed annular elements so arranged as to surround the stent axis, each of said annular elements is elongate in the axial direction of said stent and has an opening in a central portion thereof, adjacent portions of said annular elements are joined to each other through a joint, adjacent annular units being interconnected at said joints by at least one link, said annular elements in each said annular unit are so arranged that one of each adjacent pair of said annular elements is axially offset in the axial direction of said stent relative to the other annular element of the adjacent pair of annular elements, end portions of each said annular unit are projected zigzag, said zigzag projected end portion of said annular unit is in the state of penetrating into the adjacent annular unit, each of said links has a primary axis substantially parallel to the stent axis and said joints in each said annular unit have a primary axis substantially parallel to the stent axis, each respective one of said links and the joints of the two annular units to which the respective link is connected form a straight line, wherein two or more of said links are provided between an adjacent pair of said annular units.

2. The indwelling stent according to claim 1, which comprises at least two annular units in the axial direction thereof.

3. The indwelling stent according to claim 1, wherein said annular unit comprises at least four annular elements.

4. The indwelling stent according to claim 1, further comprising a radiopaque material-made marker.

5. The indwelling stent according to claim 1, wherein each said link is so disposed as not to be continuous with the adjacent link.

6. The indwelling stent according to claim 1, wherein said annular elements are not aligned substantially rectilinearly with respect to the axial direction of said stent.

7. The indwelling stent according to claim 1, wherein an end portion, located on the outer side, of each of said annular elements located at both ends of said stent is roughly semi-elliptic in shape.

8. The indwelling stent according to claim 1, which has been produced with a predetermined outside diameter by use of a plastically deformable material-made pipe and then reduced in diameter by compressing from outside.

9. An indwelling stent formed in a substantially tubular shape, having a diameter allowing for insertion into a living organism and expandable when radially outward forces are exerted thereon from the inside of the tubular shape, wherein said stent comprises annular units arranged in an axial direction of said stent, each of said annular units comprises a plurality of collapsed annular elements so arranged as to surround the stent axis, each of said annular elements is elongate in the axial direction of said stent and has an opening in a central portion thereof, adjacent portions of said annular elements are joined to each other through a joint, adjacent annular units being interconnected at said joints by at least one link, said annular elements in each said annular unit are so arranged that one of each adjacent pair of said annular elements is axially offset in the axial direction of said stent relative to the other annular element of the adjacent pair of annular elements, end portions of each said annular unit are projected zigzag, said zigzag projected end portion of said annular unit is in the state of penetrating into the adjacent annular unit, each of said links has a primary axis substantially parallel to the stent axis, and said joints in each said annular unit have a primary axis substantially parallel to the stent axis, each respective one of said links and the joints of the two annular units to which the respective link is connected form a straight line, wherein said annular elements are aligned substantially rectilinearly with respect to the axial direction of said stent.

10. The indwelling stent according to claim 9, wherein two or more said links are provided between an adjacent pair of said annular units.

11. A living organ dilator comprising a tubular shaft main body, a foldable and expandable balloon provided at a distal end portion of said shaft main body, and a stent so mounted as to envelop said balloon in a folded state and expandable by expanding said balloon, wherein said stent is an indwelling stent formed in a substantially tubular shape, having a diameter allowing for insertion into a living organism and expandable when radially outward forces are exerted thereon from the inside of the tubular shape, and said stent comprises annular units arranged in an axial direction of said stent, each of said annular units comprises a plurality of collapsed annular elements so arranged as to surround the stent axis, each of said annular elements is elongate in the axial direction of said stent and has an opening in a central portion thereof, adjacent portions of said annular elements are joined to each other through a joint, adjacent annular units being interconnected at said joints by at least one link, said annular elements in each said annular unit are so arranged that one of each adjacent pair of said annular elements is axially offset in the axial direction of said stent relative to the other annular element of the adjacent pair of annular elements, end portions of each said annular unit are projected zigzag, said zigzag projected end portion of said annular unit is in the state of penetrating into the adjacent annular unit, each of said links has a primary axis substantially parallel to the stent axis, and said joints in each said annular unit have a primary axis substantially parallel to the stent axis, each respective one of said links and the joints of the two annular units to which the respective link is connected form a straight line, wherein two or more of said links are provided between an adjacent pair of said annular units.

12. The living organ dilator according to claim 11, wherein said stent has been produced with a predetermined outside diameter by use of a plastically deformable material-made pipe, then said balloon has been disposed inside said stent, and thereafter said stent has been reduced in diameter by compressing from outside so as to mount said stent on said balloon.

13. The living organ dilator according to claim 11, wherein said annular unit of said stent comprises at least four annular elements.

14. The living organ dilator according to claim 11, wherein said stent has a radiopaque material-made marker.

15. The living organ dilator according to claim 11, wherein each said link of said stent is so disposed as not to be continuous with the adjacent link.

16. An indwelling stent formed in a substantially tubular shape, having a diameter allowing for insertion into a living organism and expandable when radially outward forces are exerted thereon from the inside of the tubular shape, said stent comprising annular units arranged in an axial direction of said stent, each of said annular units comprising a plurality of collapsed annular elements so arranged as to surround the stent axis, each of said annular elements being elongate in the axial direction of said stent and possessing an opening in a central portion thereof, adjacent portions of said annular elements in each of said annular units being joined to each other through a joint, with each adjacent pair of annular units being interconnected by at least two links, at least one link being connected to one of the joints connecting adjacent annular elements in one annular unit and one of the joints connecting adjacent annular elements in an adjacent annular unit, said annular elements in each annular unit being so arranged that one of the annular elements of each adjacent pair of said annular elements is axially offset in the axial direction of said stent relative to the other annular element of the adjacent pair of annular elements, the adjacent annular units being positioned relative to one another such that an end portion of each of a plurality of annular elements in one annular unit is positioned between end portions of two annular elements of the adjacent annular unit, wherein said at least one link has a primary axis substantially parallel to the stent axis and said joints in each of said annular units have a primary axis substantially parallel to the stent axis, and said at least one link forms a straight line with said one joint connecting adjacent annular elements in the one annular unit and said one joint connecting adjacent annular elements in the adjacent annular unit.

17. The indwelling stent according to claim 16, wherein the link connecting first and second adjacent annular units is circumferentially shifted relative to the link connecting second and third adjacent annular units.

* * * * *